US008058404B2

(12) United States Patent
Malinowski et al.

(10) Patent No.: US 8,058,404 B2
(45) Date of Patent: Nov. 15, 2011

(54) MCM6 AND MCM7 MONOCLONAL ANTIBODIES AND METHODS FOR THEIR USE IN THE DETECTION OF CERVICAL DISEASE

(75) Inventors: Douglas P. Malinowski, Hillsborough, NC (US); Timothy J. Fischer, Raleigh, NC (US); Adriann J. Taylor, Durham, NC (US)

(73) Assignee: Tripath Imaging, Inc., Burlington, NC (US)

( * ) Notice: Subject to any disclaimer, the term of this patent is extended or adjusted under 35 U.S.C. 154(b) by 197 days.

(21) Appl. No.: 12/177,481

(22) Filed: Jul. 22, 2008

(65) Prior Publication Data

US 2008/0305491 A1 Dec. 11, 2008

Related U.S. Application Data

(62) Division of application No. 11/501,391, filed on Aug. 9, 2006, now Pat. No. 7,632,498.

(60) Provisional application No. 60/751,495, filed on Dec. 19, 2005.

(51) Int. Cl.
C07K 16/18 (2006.01)
C12N 5/12 (2006.01)
(52) U.S. Cl. ............... 530/388.1; 435/7.1; 435/326
(58) Field of Classification Search ............ 435/326, 435/70.21; 530/350, 388.1
See application file for complete search history.

(56) References Cited

U.S. PATENT DOCUMENTS

| | | | |
|---|---|---|---|
| 5,858,683 A | 1/1999 | Keesee et al. | |
| 6,303,323 B1 | 10/2001 | Laskey et al. | |
| 2003/0087270 A1 | 5/2003 | Schlegel et al. | |
| 2003/0219726 A1 | 11/2003 | Doorbar | |
| 2004/0202996 A1 | 10/2004 | Williams et al. | |
| 2005/0260566 A1* | 11/2005 | Fischer et al. ............ | 435/5 |

FOREIGN PATENT DOCUMENTS

| | | |
|---|---|---|
| WO | WO 99/21014 | 4/1999 |
| WO | WO 02/101075 A2 | 12/2002 |
| WO | WO 2004/013632 A1 | 2/2004 |
| WO | WO 2005/095964 A2 | 10/2005 |

OTHER PUBLICATIONS

ATCC search output for PTA-6911 (p. 1; May 4, 2010).*
Hiraiwa, A., et al., "Immunolocalization of hCDC47 Protein in Normal and Neoplastic Human Tissues and its Relation to Growth," *Int. J. Cancer*, 1997, pp. 180-184, vol. 74.
Williams, G., et al., "Improved Cervical Smear Assessment Using Antibodies Against Proteins that Regulate DNA Replication," *Proc. Natl. Acad. Sci.*, 1998, pp. 14932-14937, vol. 95.
CDC47 / MCM7 Ab2 Data Sheet, Lab Vision, pp. 1-3, (Feb. 27, 2008).
Neomarkers Data Sheets for MCM7, Lab Vision, pp. 1-2, (Feb. 27, 2008).
Campbell et al., Biology, Fifth Edition, 1999, p. 856.
Brake, T., et al., "Comparative Analysis of Cervical Cancer in Women and in a Human Papillomavirus-Transgenic Mouse Model: Identification of *Minichromosome Maintenance Protein 7* as an Informative Biomarker for Human Cervical Cancer", *Cancer Research*, Dec. 2003, pp. 8173-8180, vol. 63.
Freeman, A., et al., "Minichromosome Maintenance Proteins as Biological Markers of Dysplasia and Malignancy," *Clinical Cancer Research*, 1999, pp. 2121-2132, vol. 5.
Grunicke, H.H., et al., "Role and Characterization of Protein Kinase C Isoforms Implicated in the Transcriptional Activation of Cyclin D1 by Transforming HA-RAS", *Cell Biology International*, 2001, pp. A16-A17, vol. 25.
Heidebrecht, H.J., et al. "Ki-Mcm6 a Monoclonal Antibody Specific for the Human Minichromosome Maintenance Protein 6 (Mcm6)", *Joint Annual Meeting*, 2000, p. 406, University of Kiel and University of Hamburg, Germany.
Helfenstein, A., et al., "Minichromosome Maintenance Protein (MCM6) in Low-Grade Chondrosarcoma", *Am. J. Clin. Pathology*, 2004, pp. 912-918, vol. 122.
Ishimi, Y., et al , "Enhanced Expression of Mcm Proteins in Cancer Cells Derived from Uterine Cervix", *Eur. J. Biochem.*, Feb. 2003, pp. 1089-1101, vol. 270.
Lederman, S., "A Single Amino Acid Substitution in a Common African Allele of the CD4 Molecule Ablates Binding of the Monoclonal Antibody, OKT4," *Molecular Immunology*, 1991, pp. 1171-1181, vol. 28(11).
Li, C.H., et al., "β-Endorphin Omission Analogs: Dissociation of Immunoreactivity From Other Biological Activities," *Proc. Natl. Acad. Sci.*, 1980, pp. 3211-3214, vol. 77(6).
Malinowski, D.P., "Molecular diagnostic Assays for Cervical Neoplasia: Emerging Markers for the Detection of High-Grade Cervical Disease", *BioTechniques*, Apr. 2005, pp. 17-23, vol. 38.
Paul, W.E., *Fundamental Immunology*, 1993, vol. 242.
Schrader, C., et al., "Minichromosome Maintenance Protein 6, a Proliferation Marker Superior to Ki-67 and Independent Predictor of Survival in Patients with Mantle Cell Lymphoma", *British Journal of Cancer*, 2005, pp. 939-945, vol. 93.
Heidebrecht, H.J., et al., "MCM6 Distribution in Proliferating Cells Detected by the Novel MAB KI-MCM6," *Cell Biology International*, 2001, pp. A16-A17, vol. 25(2).

(Continued)

*Primary Examiner* — Lynn Bristol
(74) *Attorney, Agent, or Firm* — Alston & Bird LLP

(57) ABSTRACT

Compositions and methods for diagnosing high-grade cervical disease in a patient sample are provided. The compositions include novel monoclonal antibodies, and variants and fragments thereof, that specifically bind to MCM6 or MCM7. Monoclonal antibodies having the binding characteristics of an MCM6 or MCM7 antibody of the invention are further provided. Hybridoma cell lines that produce an MCM6 or MCM7 monoclonal antibody of the invention are also disclosed herein. The compositions find use in practicing methods for diagnosing high-grade cervical disease comprising detecting overexpression of MCM6, MCM7, or both MCM6 and MCM7 in a cervical sample from a patient. Kits for practicing the methods of the invention are further provided. Polypeptides comprising the amino acid sequence for an MCM6 or an MCM7 epitope and methods of using these polypeptides in the production of antibodies are also encompassed by the present invention.

13 Claims, No Drawings

OTHER PUBLICATIONS

Heidebrecht, H.J., et al., "Ki-Mcm6, a New Monoclonal Antibody Specific to Mcm6: Comparison of the Distribution Profile of Mcm6 and the Ki-67 Antigen," *Laboratory Investigation*, 2001, pp. 1163-1165, vol. 81(8).

NCBI GenBank Report for Accession No. NP_005906, Direct Submission on Mar. 2, 2005.

Li, H., et al., "Abstract #4886—Quantitative Molecular Analysis of MCM-6 as a Specific Biomarker for Cervical Disease Diagnosis," *Proc. Amer. Assoc. Cancer Res.*, 2005, vol. 46.

Chen, Y., et al., "Identification of Cervical Cancer Markers by cDNA and Tissue Microarrays," *Cancer Research*, 2003, pp. 1927-1935, vol. 63.

\* cited by examiner

MCM6 AND MCM7 MONOCLONAL ANTIBODIES AND METHODS FOR THEIR USE IN THE DETECTION OF CERVICAL DISEASE

CROSS REFERENCE TO RELATED APPLICATIONS

This application is a divisional of U.S. application Ser. No. 11/501,391, filed Aug. 9, 2006, now U.S. Pat. No. 7,632,498, issued Dec. 15, 2009, which claims the benefit U.S. Provisional Application Ser. No. 60/751,495, filed Dec. 19, 2005, which is incorporated herein by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 346503SequenceListing.txt, a creation date of Jul. 22, 2008, and a size of 47 KB. The sequence listing filed via EFS-Web is part of the specification and is hereby incorporated in its entirety by reference herein.

FIELD OF THE INVENTION

The invention relates to antibodies capable of binding to MCM6 or MCM7 and methods of using these antibodies, particularly in the diagnosis of cervical disease.

BACKGROUND OF THE INVENTION

Carcinoma of the cervix is the second most common neoplasm in women, accounting for approximately 12% of all female cancers and causing approximately 250,000 deaths per year. Baldwin et al. (2003) *Nature Reviews Cancer* 3: 1-10. In many developing countries where mass screening programs are not available, the clinical problem is more serious. Cervical cancer in these countries is the number one cause of cancer deaths in women.

The majority of cases of cervical cancer represent squamous cell carcinoma, although adenocarcinoma is also seen. Cervical cancer can be prevented by population screening as it evolves through well-defined noninvasive intraepithelial stages, which can be distinguished morphologically. Williams et al. (1998) *Proc. Natl. Acad. Sci. USA* 95:14932-14937. While it is not understood how normal cells become transformed, the concept of a continuous spectrum of histopathological change from normal, stratified epithelium through cervical intraepithelial neoplasia (CIN) to invasive cancer has been widely accepted for years. The precursor to cervical cancer is dysplasia, also known in the art as CIN or squamous intraepithelial lesions (SIL). Squamous intraepithelial abnormalities may be classified by using the three-tiered (CIN) or two-tiered (Bethesda) system. Under the Bethesda system, low-grade squamous intraepithelial lesions (LSIL), corresponding to CINI and HPV infection, generally represent productive HPV infections with a relatively low risk of progression to invasive disease. High-grade squamous intraepithelial lesions (HSIL), corresponding to CINII and CINIII in the three-tiered system, show a higher risk of progression to cervical cancer than do LSIL, although both LSIL and HSIL are viewed as potential precursors of malignancy. Patient samples may also be classified as ASCUS (atypical squamous cells of unknown significance) or AGUS (atypical glandular cells of unknown significance) under this system.

A strong association of cervical cancer and infection by high-risk types of human papilloma virus (HPV), such as types 16, 18, and 31, has been established. In fact, a large body of epidemiological and molecular biological evidence has established HPV infection as a causative factor in cervical cancer. Moreover, HPV is found in 85% or more of the cases of high-grade cervical disease. However, HPV infection is very common, possibly occurring in 5-15% of women over the age of 30, but few HPV-positive women will ever develop high-grade cervical disease or cancer. The presence of HPV alone is indicative only of infection, not of high-grade cervical disease, and, therefore, testing for HPV infection alone results in many false positives. See, for example, Wright et al. (2004) *Obstet. Gynecol.* 103:304-309.

Current literature suggests that HPV infects the basal stem cells within the underlying tissue of the uterine-cervix. Differentiation of the stem cells into mature keratinocytes, with resulting migration of the cells to the stratified cervical epithelium, is associated with HPV viral replication and re-infection of cells. During this viral replication process, a number of cellular changes occur that include cell-cycle de-regulation, active proliferation, DNA replication, transcriptional activation and genomic instability (Crum (2000) *Modern Pathology* 13:243-251; Middleton et al. (2003) *J. Virol.* 77:10186-10201; Pett et al. (2004) *Cancer Res.* 64:1359-1368).

Most HPV infections are transient in nature, with the viral infection resolving itself within a 12-month period. For those individuals who develop persistent infections with one or more oncogenic subtypes of HPV, there is a risk for the development of neoplasia in comparison to patients without an HPV infection. Given the importance of HPV in the development of cervical neoplasia, the clinical detection of HPV has become an important diagnostic tool in the identification of patients at risk for cervical neoplasia development. The clinical utility of HPV-based screening for cervical disease is in its negative predictive value. An HPV negative result in combination with a history of normal Pap smears is an excellent indicator of a disease-free condition and a low risk of cervical neoplasia development during the subsequent 1-3 years. However, a positive HPV result is not diagnostic of cervical disease; rather it is an indication of infection. Although the majority of HPV infections is transient and will spontaneously clear within a 12-month period, a persistent infection with a high-risk HPV viral subtype indicates a higher risk for the development of cervical neoplasia. To supplement HPV testing, the identification of molecular markers associated with cervical neoplasia is expected to improve the clinical specificity for cervical disease diagnosis.

Cytological examination of Papanicolaou-stained cervical smears (Pap smears) currently is the method of choice for detecting cervical cancer. The Pap test is a subjective method that has remained substantially unchanged for 60 years. There are several concerns, however, regarding its performance. The reported sensitivity of a single Pap test (the proportion of disease positives that are test-positive) is low and shows wide variation (30-87%). The specificity of a single Pap test (the proportion of disease negatives that are test-negative) might be as low as 86% in a screening population and considerably lower in the ASCUS PLUS population for the determination of underlying high-grade disease. See, Baldwin et al., supra. A significant percentage of Pap smears characterized as LSIL or CINI are actually positive for high-grade lesions. Furthermore, up to 10% of Pap smears are classified as ASCUS (atypical squamous cells of undetermined significance), i.e., it is not possible to make a clear categorization as normal, moderate or severe lesion, or tumor. However, experience shows that up to 10% of this ASCUS population has high-grade lesions, which are consequently overlooked. See, for example, Manos et al. (1999) *JAMA* 281:1605-1610. Therefore, molecular biomarkers that are selectively overexpressed in high-grade cervical disease and compositions for the detection of these biomarkers are needed to practice reliable methods for diagnosing high-grade cervical disease.

Minichromosome maintenance (MCM) proteins play an essential part in eukaryotic DNA replication. The minichromosome maintenance (MCM) proteins function in the early stages of DNA replication through loading of the prereplication complex onto DNA and functioning as a helicase to help unwind the duplex DNA during de novo synthesis of the duplicate DNA strand. Each of the MCM proteins has DNA-dependent ATPase motifs in their highly conserved central domain. Levels of MCM proteins generally increase in a variable manner as normal cells progress from G0 into the G1/S phase of the cell cycle. In the G0 phase, MCM2 and MCM5 proteins are much less abundant than are the MCM7 and MCM3 proteins. MCM6 forms a complex with MCM2, MCM4, and MCM7, which binds histone H3. In addition, the subcomplex of MCM4, MCM6, and MCM7 has helicase activity, which is mediated by the ATP-binding activity of MCM6 and the DNA-binding activity of MCM4. See, for example, Freeman et al. (1999) *Clin. Cancer Res.* 5:2121-2132; Lei et al. (2001) *J. Cell Sci.* 114:1447-1454; Ishimi et al. (2003) *Eur. J. Biochem.* 270:1089-1101, all of which are herein incorporated by reference in their entirety.

Early publications have shown that the MCM proteins, and in particular, MCM5, are useful for the detection of cervical disease (Williams et al. (1998) *Proc Natl Acad Sci U.S.A.* 95:14932-14937), as well as other cancers (Freeman et al. (1999) *Clin Cancer Res.* 5:2121-2132). The published literature indicates that antibodies to MCM5 are capable of detecting cervical neoplastic cells. The specificity for detection of high-grade cervical disease has not been demonstrated for MCM5 (Williams et al. (1998) *Proc Natl Acad Sci U.S.A.* 95:14932-14937). The detection of MCM5 expression is not restricted to high-grade cervical disease but is also detected in identified low-grade dysplasia and proliferative cells that have re-entered the cell cycle following infection with high-risk HPV. In addition to MCM5, other members from the MCM family, including MCM2 and MCM7 have been shown to be potentially useful markers for the detection of cervical neoplasia in tissue samples (Freeman et al. (1999) *Clin Cancer Res.* 5:2121-2132; Brake et al. (2003) *Cancer Res.* 63:8173-8180). Recent results have shown that MCM7 appears to be a specific marker for the detection of high-grade cervical disease using immunochemistry formats (Brake et al. (2003) *Cancer Res.* 63:8173-8180; Malinowski et al. (2004) *Acta Cytol.* 43:696).

Therefore, there is a need in the art for antibodies that are capable of detecting expression of a biomarker that is selectively overexpressed in high-grade cervical disease. Such antibodies could be used in methods for differentiating high-grade disease from conditions that are not considered clinical disease, such as early-stage HPV infection and mild dysplasia.

SUMMARY OF THE INVENTION

Compositions and methods for diagnosing high-grade cervical disease are provided. Compositions include monoclonal antibodies capable of binding to nuclear biomarker proteins of the invention, particularly MCM proteins, more particularly MCM6 and MCM7. Antigen-binding fragments and variants of these monoclonal antibodies, hybridoma cell lines capable of producing these antibodies, and kits comprising the monoclonal antibodies of the invention are also encompassed herein.

The compositions of the invention find use in methods for diagnosing high-grade cervical disease. The methods comprise detecting expression of at least one nuclear biomarker, wherein overexpression of the nuclear biomarker is indicative of high-grade cervical disease. Specifically, the methods comprise using the antibodies of the invention to detect overexpression of MCM6 or MCM7 in a cervical sample.

Compositions of the invention further include isolated polypeptides that comprise an epitope capable of binding an MCM6 or MCM7 monoclonal antibody. These polypeptides find use in methods for producing MCM6 or MCM7 antibodies. Isolated nucleic acid molecules encoding the amino acid sequences of the MCM6 or MCM7 epitopes are also provided.

DETAILED DESCRIPTION OF THE INVENTION

Compositions and methods for diagnosing high-grade cervical disease are provided. Compositions include monoclonal antibodies that are capable of binding to nuclear biomarker proteins that are selectively overexpressed in high-grade cervical disease, particularly MCM proteins, more particularly MCM6 and MCM7. Hybridoma cell lines that produce the monoclonal antibodies of the present invention are also disclosed. Kits comprising the monoclonal antibodies described herein are further provided. The present compositions find use in methods for diagnosing high-grade cervical disease in a patient.

The compositions of the invention include monoclonal antibodies that specifically bind to MCM6 or MCM7, or to a variant or fragment thereof. The amino acid and nucleotide sequences for MCM6 are set forth in SEQ ID NO:3 (Accession No. NP_005906) and SEQ ID NO:4 (Accession No. NM_005915), respectively. The amino acid and nucleotide sequences for MCM7 are set forth in SEQ ID NO:1 (Accession No. NP_005907) and SEQ ID NO:2 (Accession No. NM_005916), respectively. In particular embodiments, the MCM6 monoclonal antibody designated as 9D4.3 and the MCM7 monoclonal antibody designated as 2E6.2 are provided. A hybridoma cell line that produces MCM7 monoclonal antibody 2E6.2 was deposited with the Patent Depository of the American Type Culture Collection (ATCC), Manassas, Va., 20110-2209 on Apr. 14, 2005 and assigned Patent Deposit No. PTA-6669. A hybridoma cell line that produces MCM6 monoclonal antibody 9D4.3 was deposited with the Patent Depository of the American Type Culture Collection (ATCC), Manassas, Va., 20110-2209 on Aug. 9, 2005 and assigned Patent Deposit No. PTA-6911. These deposits will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. §112.

Antibodies that have the binding characteristics of monoclonal antibody 9D4.3 and 2E6.2 are also disclosed herein. Such antibodies include, but are not limited to, antibodies that compete in competitive binding assays with these antibodies, as well as antibodies that bind to an epitope capable of binding monoclonal antibody 9D4.3 or 2E6.2. Variants and fragments of monoclonal antibody 9D4.3 and 2E6.2 that retain the ability to specifically bind to MCM6 or MCM7, respectively, are also provided. Compositions further include hybridoma cell lines that produce the monoclonal antibodies of the present invention and kits comprising at least one monoclonal antibody disclosed herein.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. As used herein, "MCM6 antibody" or "MCM7 antibody" refers to any antibody that specifically binds to MCM6 (SEQ ID NO:3) or MCM7 (SEQ ID NO:1), or to a variant or fragment thereof, and includes monoclonal antibodies, polyclonal antibodies, single-chain antibodies, and fragments thereof which retain the antigen binding function of the parent antibody.

The MCM6 and MCM7 antibodies of the invention are optimally monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (V,) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy-chain variable domains. The more highly conserved portions of variable domains are called the framework (FR) regions. The variable domains of native heavy and light chains each comprise four FR regions, largely adopting a p-sheet configuration, connected by three CDRs, which form loops connecting, and 15 in some cases forming part of, the p-sheet structure. The CDRs in each chain are held together in close proximity: by the FR regions and, with the CDRs from the other chain, contribute to the formation of the antigen-binding site: of antibodies (see Kabat et al., NIH Publ. No. 91-3242, Vol. I, pages 647-669 (1991)).

The constant domains are not involved directly in binding an antibody to an antigen, but exhibit various effecter functions, such as participation of the antibody in antibody-dependent cellular toxicity.

The term "hypervariable region" when used herein refers to the amino acid residues of an antibody which: are responsible for antigen-binding. The hypervariable region comprises amino acid residues from a "complementarily determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institute of Health, 25 Bethesda, Md. [1991]) and/or those residues from a "hypervariable loop" (i.e., residues 26-32 (L1), 50-52 (L2) and 91-96 (L3) in the light chain variable domain and 2632(H1), 53-55 (H2) and 96-101 (H3) in the heavy chain variable domain; Clothia and Lesk, J. Mol. Biol., 196:901-917 [1987]). Framework" or "FR" residues are those variable domain residues other than the hypervariable region residues as herein deemed.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Fragments of the MCM6 and MCM7 antibodies are encompassed by the invention so long as they retain the desired affinity of the full-length antibody. Thus, for example, a fragment of an MCM6 antibody will retain the ability to bind to an MCM6 antigen. Similarly, a fragment of an MCM7 antibody will retain the ability to bind to an MCM7 antigen. Such fragments are characterized by properties similar to the corresponding full-length antibody, that is, the fragments will specifically bind MCM6 or MCM7. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Preferably antibodies of the invention are monoclonal in nature. As indicated above, "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site, i.e., a particular epitope within the MCM6 or MCM7 protein, as defined herein below. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen (i.e., antibody-producing cells) bind to the plate and are not rinsed away. Resulting B cells, or all dissociated spleen cells, are then induced to fuse with myeloma cells to form monoclonal antibody-producing hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice). Monoclonal antibodies can also be produced using Repetitive Immunizations Multiple Sites technology (RIMMS). See, for example, Kilpatrick et al. (1997) *Hybridoma* 16(4):381-389; Wring et al. (1999) *J. Pharm. Biomed. Anal.* 19(5):695-707; and Bynum et al. (1999) *Hybridoma* 18(5):407-411, all of which are herein incorporated by reference in their entirety.

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody. A monoclonal antibody can also be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene *SurfZAP ʃ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

In some aspects of the invention, antibodies may be selected on the basis of desirable staining of cytological, rather than histological, samples. That is, in particular embodiments the antibodies are selected with the end sample type (e.g., cytology preparations) in mind and for binding specificity. Antibodies directed to specific biomarkers of interest, such as MCM6 or MCM7, are selected and purified via a multi-step screening process. Such methods for antibody selection are described in pending U.S. application Ser. No. 11/087,227, entitled "Methods and Compositions for the Detection of Cervical Disease," filed Mar. 23, 2005, which is herein incorporated by reference in its entirety.

Antibodies having the binding characteristics of a monoclonal antibody of the invention are also provided. "Binding characteristics" or "binding specificity" when used in reference to an antibody means that the antibody recognizes the same or similar antigenic epitope as a comparison antibody. Examples of such antibodies include, for example, an antibody that competes with a monoclonal antibody of the invention in a competitive binding assay. One of skill in the art could determine whether an antibody competitively interferes with another antibody using standard methods.

By "epitope" is intended the part of an antigenic molecule to which an antibody is produced and to which the antibody will bind. An "MCM6 epitope" comprises the part of the MCM6 protein to which an MCM6 monoclonal antibody binds. An "MCM7 epitope" comprises the part of the MCM7 protein to which an MCM7 monoclonal antibody binds. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues. Typically epitopes are short amino acid sequences, e.g. about five amino acids in length. Systematic techniques for identifying epitopes are known in the art and are described, for example, in U.S. Pat. No. 4,708,871 and in the examples set forth below. Briefly, in one method, a set of overlapping oligopeptides derived from the antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to a biomarker-specific monoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained.

The invention also encompasses isolated polypeptides comprising an epitope for binding an MCM6 or MCM7 monoclonal antibody. These polypeptides correspond to a portion of the antigen (i.e., MCM6 or MCM7) that binds to a monoclonal antibody. Such polypeptides find use in methods for producing antibodies that bind selectively to MCM6 or MCM7. The ability of a polypeptide to be used in the production of antibodies is referred to herein as "antigenic activity." For example, the amino acid sequence set forth in SEQ ID NO:5 (corresponding to residues 760-772 in the MCM6 amino acid sequence set forth in SEQ ID NO:3) comprise an epitope recognized by an MCM6 monoclonal antibody, more particularly monoclonal antibody 9D4.3. The amino acid sequence set forth in SEQ ID NO:6 (corresponding to residues 127-138 in the MCM7 amino acid sequence set forth in SEQ ID NO:1) comprise an epitope recognized by an MCM7 monoclonal antibody, more particularly monoclonal antibody 2E6.2. Variants and fragments of the MCM6 and MCM7 epitope sequences set forth in SEQ ID NOs:5 and 6 that retain the antigenic activity of the original polypeptide are also provided. The invention further includes isolated nucleic acid molecules that encode polypeptides that comprise MCM6 or MCM7 epitopes, and variants and fragments thereof.

The polypeptides of the invention comprising MCM6 or MCM7 epitopes can be used in methods for producing monoclonal antibodies that specifically bind to MCM6 or MCM7, as described herein above. Such polypeptides can also be used in the production of polyclonal MCM6 or MCM7 antibodies. For example, polyclonal antibodies can be prepared by immunizing a suitable subject (e.g., rabbit, goat, mouse, or other mammal) with a polypeptide comprising an MCM6 or MCM7 epitope (i.e., an immunogen). The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550-52; Kenneth (1980) in *Monoclonal Antibodies: A New Dimension In Biological Analyses* (Plenum Publishing Corp., NY; and Lerner (1981) *Yale J. Biol. Med.*, 54:387-402).

Amino acid sequence variants of a monoclonal antibody or a polypeptide comprising an MCM6 or MCM7 epitope described herein are also encompassed by the present invention. Variants can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the polypeptide of interest, modifications are made such that variants continue to possess the desired activity, i.e., similar binding affinity to the biomarker. Obviously, any mutations made in the DNA encoding the variant polypeptide must not place the sequence out of reading frame and preferably will not create complementary regions that could produce secondary mRNA structure. See EP Patent Application Publication No. 75,444.

Preferably, variants of a reference polypeptide have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody molecule, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The MCM6 and MCM7 monoclonal antibodies of the invention may be labeled with a detectable substance as described below to facilitate biomarker protein detection in the sample. Such antibodies find use in practicing the methods of the invention. The antibodies and antibody fragments of the invention can be coupled to a detectable substance to facilitate detection of antibody binding. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Examples of detectable substances for purposes of labeling antibodies include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Kits comprising at least one MCM6 or one MCM7 monoclonal antibody of the invention are further provided. By "kit" is intended any manufacture (e.g., a package or a container) comprising at least one reagent, i.e., an antibody, for specifically detecting the expression of MCM6 or MCM7. The kit may be promoted, distributed, or sold as a unit for performing the methods of the present invention. Additionally, the kits may contain a package insert describing the kit and methods for its use.

Kits of the invention generally comprise at least one monoclonal antibody directed to MCM6 or MCM7, chemicals for the detection of antibody binding, a counterstain, and, optionally, a bluing agent to facilitate identification of positive staining cells. Any chemicals that detect antigen-antibody binding may be used in the kits of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. In other embodiments, antibody binding to a biomarker protein is detected through the use of a mouse probe reagent that binds to monoclonal antibodies, followed by addition of a dextran polymer conjugated with HRP that binds to the mouse probe reagent. Such detection reagents are commercially available from, for example, Biocare Medical.

The kits of the present invention may further comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with Tween-20 and sodium azide) may be further provided in the kit to facilitate detection of positive staining cells. Kits may also comprise positive and negative control samples for quality control purposes.

In another embodiment, the kits of the invention comprise at least two monoclonal antibodies. In certain aspects of the invention, the kits comprise an MCM6 and an MCM7 antibody, more particularly the MCM6 monoclonal antibody 9D4.3 and the MCM7 antibody 2E6.2. When multiple antibodies are present in the kit, each antibody may be provided as an individual reagent or, alternatively, as an antibody cocktail comprising all of the antibodies of interest. Furthermore, any or all of the kit reagents may be provided within containers that protect them from the external environment, such as in sealed containers. The kits of the invention are useful in the diagnosis of high-grade cervical disease and may further include reagents for Pap staining (e.g., EA50 and Orange G).

The compositions of the invention find use in methods for diagnosing high-grade cervical disease in a patient such as those disclosed in pending U.S. application Ser. No. 11/087,227, entitled "Methods and Compositions for the Detection of Cervical Disease," filed Mar. 23, 2005, which is herein incorporated by reference in its entirety. "Diagnosing high-grade cervical disease" is intended to include, for example, diagnosing or detecting the presence of cervical disease, monitoring the progression of the disease, and identifying or detecting cells or samples that are indicative of high-grade cervical disease. The terms diagnosing, detecting, and identifying high-grade cervical disease are used interchangeably herein. By "high-grade cervical disease" is intended those conditions classified by colposcopy as premalignant pathology, malignant pathology, moderate to severe dysplasia, and cervical cancer. Underlying high-grade cervical disease includes histological identification of CINII, CINIII, HSIL, carcinoma in situ, adenocarcinoma, and cancer (FIGO stages I-IV).

The methods of the invention comprise detecting overexpression of at least one nuclear biomarker that is selectively overexpressed in high-grade cervical disease. By "nuclear biomarker" is intended any gene of protein that is predominantly expressed in the nucleus of the cell. A nuclear biomarker may be expressed to a lesser degree in other parts of the cell. By "selectively overexpressed in high-grade cervical disease" is intended that the nuclear biomarker of interest is overexpressed in high-grade cervical disease but is not overexpressed in conditions classified as LSIL, CINI, HPV-infected samples without any dysplasia present, immature metaplastic cells, and other conditions that are not considered to be clinical disease. Thus, detection of the nuclear biomarkers of the invention permits the differentiation of samples indicative of underlying high-grade cervical disease from samples that are indicative of benign proliferation, early-stage HPV infection, or mild dysplasia. Nuclear biomarkers of particular interest include MCM proteins, particularly MCM6 and MCM7.

In a particular aspect of the invention, the methods comprise obtaining a cervical sample from a patient, contacting the sample with at least one MCM6 or MCM7 monoclonal antibody of the invention, and detecting binding of the antibody to the MCM protein. In other embodiments, the sample is contacted with at least two monoclonal antibodies, a first antibody that specifically binds to MCM6, particularly monoclonal antibody 9D4.3, and a second antibody that specifically binds to MCM7, particularly monoclonal antibody 2E6.2. Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. Any method for detecting antibody-antigen binding may used to practice the methods of the invention.

Clarification of Supernatant

Turn on the tabletop centrifuge. Place the 500 ml tube adapters into the rotor buckets, close the lid and set the temperature to 4° C. (+/−) 4° C.

Using aseptic technique, pour the media from all four of the now exhausted T-225 flasks into 2×500 ml conical centrifuge tubes.

Make sure the 2×500 ml tubes are balanced. Transfer supernatant from one tube to the other as necessary to balance them.

Centrifuge the exhausted supernatant at 1350 g (+/−40 g) for 15 minutes at 2° C. to 10° C.

After centrifugation is complete, aseptically decant the supernatant into a sterile 1000 ml storage bottle and secure with a sterile cap.

Aseptically transfer 1 ml to the microfuge tube. Store microfuge tube with sample at 2° C. to 10° C. (Protect from light).

The clarified supernatant sample is ready for IgG evaluation using the antibody assay, EASY-TITER® Assay.

One of skill in the art will appreciate that any or all of the steps in the methods of the invention could be implemented by personnel in a manual or automated fashion. Thus, the steps of cervical sample preparation, antibody, and detection of antibody binding may be automated. The methods of the invention may also be combined with conventional Pap staining techniques to permit a more accurate diagnosis of high-grade cervical disease.

The following examples are offered by way of illustration and not by way of limitation:

EXPERIMENTAL

Example 1

Production of Mouse Monoclonal Antibodies to MCM7

Mouse monoclonal antibodies specific for MCM7 were generated. The antigen (an immunogenic polypeptide) was a recombinant hexahistidine-tagged N-terminal fragment of the MCM7 protein. The antigen was expressed using a baculovirus expression system in Tni cells. Specifically, the coding sequence for the hexahistidine-tagged MCM7 N-terminal fragment (SEQ ID NO:7) was cloned into the pFastBac1 plasmid (Invitrogen) for expression in Tni cells. Methods for producing recombinant proteins using baculovirus expression systems are well known in the art. The tagged MCM7 fragment was purified using a chelating agarose charged with Ni+2 ions (Ni-NTA from Qiagen) and used as an immunogen. The amino acid sequence of the immunogenic MCM7 N-terminal polypeptide fragment is provided in SEQ ID NO:8.

Mouse immunizations and hybridoma fusions were performed essentially as described in Kohler et al. (1975) *Nature* 256:495-496. Mice were immunized with the immunogenic tagged-MCM7 fragment in solution. Antibody-producing cells were isolated from the immunized mice and fused with myeloma cells to form monoclonal antibody-producing hybridomas. The hybridomas were cultured in a selective medium. The resulting cells were plated by serial dilution and assayed for the production of antibodies that specifically bind MCM7 (and that do not bind to unrelated antigens). To confirm that the monoclonal antibodies of interest reacted with the MCM7 protein only and not with the hexahistidine tag, selected hybridomas were screened against an MCM7-FLAG-tagged protein. Selected monoclonal antibody (mAb)-secreting hybridomas were then cultured.

Antibodies were purified from the culture media supernatants of "exhausted" hybridoma cells (i.e., cells grown until viability drops to between 0-15%) using recombinant Protein A-coated resin (STREAMLINE™, Amersham, Inc.). Antibodies were eluted using low pH followed by immediate neutralization of pH. Fractions with significant absorbances at 280 nM were pooled. The resultant pool was dialyzed against PBS. Purified antibodies were subjected to further characterization. MCM7 monoclonal antibody 2E6.2 was determined to be an $IgG_1$ isotype. Details of the epitope mapping of this antibody are described below.

Example 2

Production of Mouse Monoclonal Antibodies to MCM6

Mouse monoclonal antibodies specific for MCM6 were generated. The antigen (an immunogenic polypeptide) was a recombinant FLAG-tagged MCM6 protein. The antigen was expressed using a proprietary expression vector from Cell & Molecular Technology, Inc. in HEK293 cells or alternatively expressed using a baculovirus expression system in Tni cells. The coding sequence for the FLAG-tagged MCM6 is set forth in SEQ ID NO:9. FLAG-tagged MCM6 was purified from cell lysates using the anti-FLAG M2 Affinity Gel matrix and the FLAG peptide for elution (Sigma Chemical Co., St. Louis, Mo.). The FLAG-tagged MCM6 protein used as an immunogen. The amino acid sequence of the immunogenic FLAG-tagged MCM6 polypeptide is provided in SEQ ID NO:10.

Mouse immunizations and lymphocyte fusion were performed by RIMMS technology, essentially as described in Kilpatrick et al. (1997) Hybridoma 16(4):381-389. Mice were immunized with the immunogenic FLAG-tagged-MCM6. Primary screening of uncloned hybridoma supernatants was performed using recombinant MCM6 protein. Secondary screening and screening of cloned hybridoma supernatants was performed using a separate batch of recombinant MCM6 protein. Selected monoclonal antibody (mAb)-secreting hybridomas were then cultured.

Antibodies were purified from the culture media supernatants of "exhausted" hybridoma cells (i.e., cells grown until viability drops to between 0-15%) using recombinant Protein A-coated resin (STREAMLINE™, Amersham, Inc.). Antibodies were eluted using low pH followed by immediate neutralization of pH. Fractions with significant absorbances at 280 nM were pooled. The resultant pool was dialyzed against PBS. Purified antibodies were subjected to further characterization. MCM6 monoclonal antibody 9D4.3 was determined to be an $IgG_{2\alpha}$ isotype. Details of the epitope mapping of this antibody are described below.

Example 3

Isolation of Monoclonal Antibodies from Hybridoma Cells

The following procedure is used to isolate monoclonal antibodies from hybridoma cells:

Media Preparation
  To a sterile 1,000 ml storage bottle, add 100 ml Hyclone Fetal Bovine Serum (FBS).
  Add 10 ml of MEM Non-Essential Amino Acids Solution.
  Add 10 ml of Penicillin-Streptomycin-L-Glutamine Solution.
  QS to approximately 1000 ml with ExCell 610-HSF media.
  Place sterile cap on bottle and secure tightly. Swirl gently to mix.
  Connect a 1000 ml sterile acetate vacuum filter unit (0.2 μm) to a vacuum pump system.
  Gently pour approximately half of the media solution into sterile acetate vacuum filter unit and turn on the vacuum.
  Once the first half of the media has been filtered, pour the remaining media into the filter unit and continue filtering.
  After all the media has been filtered, disconnect the vacuum hose from the vacuum filter unit and turn off the vacuum pump. Remove the receiver portion of the filter unit from the filter bottle. Place a new sterile bottle cap on the bottle.
  Store at 2° C. to 10° C. Protect from light.

Initial Hybridoma Cell Culture
  Thaw vial of stock hybridoma frozen culture in a pre-warmed 37° C. $H_2O$ bath.
  Spray the outside of the freeze vial with 70% ethanol.
  Move the thawed vial into the Biological Safety Cabinet.
  Remove the cells from the freeze vial and transfer the cells to a 15 ml centrifuge tube.
  Add 7 ml of cell culture media drop-wise to the 15 ml centrifuge tube containing the thawed cells.
  Centrifuge the 15 ml centrifuge tube containing the thawed cells and culture media for 5 minutes at 200 g force.
  While the cells are in the centrifuge, add 45 ml of cell culture media to a sterile T-225 flask.
  After centrifugation, visually inspect the tube for the presence of a cell pellet.
  Remove the media from the centrifuge tube being careful not to dislodge the cell pellet. Note: If the cell pellet is disturbed, repeat the centrifugation step.
  Add 5 ml of cell culture media to the 15 ml centrifuge tube containing the pelleted cells. Pipette to re-suspend the cell pellet into the media.
  Transfer the entire contents of the resuspended cells and culture media into the T-225 flask containing the 45 ml of media.
  Cap the T-225 flask.
  Observe for presence of intact cells under the microscope. Place the T-225 flask immediately into a CO2 incubator and allow the cells to incubate overnight.

Expansion of Hybridoma Cell Line
  Continue to monitor the cell culture for viability, concentration, and presence of contamination.
  Monitor and adjust the cell suspension from the initial T-225 flask until the concentration is approximately 600,000 cells/ml to 800,000 cells/ml and a total of 200 to 250 ml of media.
  Dislodge cells and add additional media as needed to meet minimum cell density requirements. Divide and transfer cell suspension into one new sterile T-225 flask. Place the 2×T-225 flasks into the CO2 incubator.
  Monitor the cells from the 2×T-225 flasks until the concentration is approximately 600,000 cells/ml to 800,000 cells/ml, and a total of between 200 to 250 ml of media for each flask.
  Dislodge cells and add additional media as needed to meet minimum cell density requirements. Divide and transfer the cell suspensions into 2 additional new sterile T-225 flasks for a total of 4×T-225 flasks. Return all flasks to the CO2 incubator.
  Monitor the cells, and adjust volume in the 4×T-225 flasks until the cell concentration is approximately 600,000 cells/ml to 800,000 cells/ml with a total volume of approximately 250 ml per T-225 flask (or approximately 1000 ml total).
  Continue to monitor the cells from the 4×T-225 flasks until the cells have grown to exhaustion, with a final viability of 0%-15%. The cell culture supernatant is now ready for the Clarification Process.

As used herein, "cervical sample" refers to any sampling of cells, tissues, or bodily fluids from the cervix in which expression of a biomarker can be detected. Examples of such body samples include but are not limited to gynecological fluids, biopsies, and smears. Cervical samples may be obtained from a patient by a variety of techniques including, for example, by scraping or swabbing an area or by using a needle to aspirate bodily fluids. Methods for collecting cervical samples are well known in the art. In particular embodiments, the cervical sample comprises cervical cells, particularly in a liquid-based preparation. In one embodiment, cervical samples are collected according to liquid-based cytology specimen preparation guidelines such as, for example, the liquid based Pap test, SUREPATH® (TriPath Imaging, Inc.) or the modified Pap test, THINPREP® preparation (CYTYC, Inc.). Cervical samples may be transferred to a glass slide for viewing under magnification. Fixative and staining solutions may be applied to the cells on the glass slide for preserving the specimen and for facilitating examination. In one embodiment the cervical sample will be collected and processed to provide a monolayer sample, as set forth in U.S. Pat. No. 5,346,831, herein incorporated by reference.

Buffer Preparation

Binding Buffer:
- Add approximately 600 ml of DI $H_2O$ to a clean beaker.
- Add 77.28 ml of Boric Acid solution (4% W/V). Stir at room temperature with a clean stir bar.
- Weigh out 233.76 g of Sodium Chloride and place into the solution while continuing to stir.
- Bring solution up to approximately 950 ml with DI $H_2O$ and continue to stir.
- When the Sodium Chloride has dissolved and the solution is clear, adjust the pH to 9.0±0.2 with Sodium Hydroxide.
- Remove the solution to a clean 1000 ml graduated cylinder and QS to 1000 ml with DI $H_2O$.
- Transfer the completed buffer to an appropriate storage bottle. This buffer may be stored for up to 7 days before use.
- Repeat this entire process to prepare an additional 0.2 liters to 1.0 liter of Binding Buffer.

Elution Buffer
- Weigh out 1.725 g of sodium phosphate, monobasic and place into a clean 250 ml beaker with a clean stir bar.
- Weigh out 3.676 g of sodium citrate and place into the same clean 250 ml beaker.
- Add approximately 175 ml of DI $H_2O$ and stir at room temperature until dissolved.
- Weigh out 4.38 g of Sodium Chloride and place into the solution while continuing to stir.
- Bring solution up to approximately 225 ml with DI $H_2O$ and continue to stir.
- When the Sodium Chloride has dissolved and the solution is clear, adjust the pH to 3.5±0.2 with Hydrochloric Acid.
- Remove the solution to a clean 250 ml graduated cylinder and QS to 250 ml with DI $H_2O$.
- Connect a 500 ml sterile acetate vacuum filter unit (0.2 µm) to a vacuum pump system and filter sterilize the solution.
- Remove the filter and close the container with a sterile cap.

Antibody Adsorption
- Pour the Clarified Supernatant (~1 L) into a clean 4000 ml plastic beaker with a clean stir bar.
- Add an approximately equal amount (~1 L) of the Binding Buffer to the clean 4000 ml plastic beaker containing the clarified supernatant. Add a clean stir bar.
- Cover the beaker with clean plastic wrap and label "Antibody Binding."
- Calculate the approximate amount of STREAMLINE® Protein A that will be needed using the data in Table 1.

TABLE 1

| Volume of Protein A Resin Required | |
|---|---|
| Quantity IgG (µg/ml) in Supernatant | Volume of Protein A Resin Required in Milliliters (ml) |
| >180-≦200 | 12.0 |
| >160-≦180 | 11.0 |
| >140-≦160 | 10.0 |
| >120-≦140 | 9.0 |
| >100-≦120 | 8.0 |
| >80-≦100 | 7.0 |
| >60-≦80 | 6.0 |
| >40-≦60 | 4.5 |
| >20-≦40 | 3.5 |
| ≦20 | 2.0 |

- Secure a clean Disposable Column and stopcock assembly to a ring stand and clamp. Close the stopcock.
- Mix appropriate amount of STREAMLINE Protein A beads by inverting the bottle several times. Withdraw the required volume and place into the Disposable Column.
- Wash the STREAMLINE Protein A beads with 10 ml of DI $H_2O$. Open the stopcock and allow the DI $H_2O$ to drain. Close the stopcock. Repeat with an additional 10 ml of DI $H_2O$.
- Wash the STREAMLINE Protein A beads with 10 ml of Binding Buffer. Open the stopcock and allow the Binding Buffer to drain. Close the stopcock. Repeat with an additional 10 ml of Binding Buffer.
- Resuspend the STREAMLINE Protein A beads in ~10 ml of the Clarified Supernatant and Binding Buffer solution (from the 4000 ml beaker) and transfer the beads into the 4000 ml beaker containing the Clarified Supernatant and Binding Buffer solution. Repeat as required to transfer any remaining beads. When completed, discard the column and stopcock.
- Allow the mixture to mix vigorously at 2° C. to 10° C. for approximately 18 hours.
- When mixing is complete, turn off the stir plate and remove the "Antibody Binding" beaker with the buffered supernatant and bead suspension back to the lab bench area. Allow the STREAMLINE Protein A beads to settle to the bottom of the beaker (approximately 5 minutes).
- Secure a clean Disposable Column and stopcock assembly to a ring stand and clamp. Close the stopcock.
- Label a clean, 250 ml bottle or suitable container "Column Wash-Post Binding."
- Label a clean plastic beaker "Supernatant-Post Binding."
- Decant the supernatant from the 4000 ml beaker into the clean, labeled, 2 liter plastic beaker, leaving the beads in the bottom of the 4000 ml beaker. Cover the 2000 ml beaker containing the "Supernatant-Post Binding" solution with clean plastic wrap and store at 2° C. to 10° C.

Add approximately 15 ml of Binding Buffer into the decanted 4000 ml "Antibody Binding" beaker. Resuspend the STREAMLINE Protein A beads and transfer them to the column. Open the stopcock and allow the Binding Buffer to drain into the "Column Wash-Post binding" container. Close the stopcock when drained.

Transfer any remaining STREAMLINE Protein A beads in the "Antibody Binding" beaker by adding additional Binding Buffer, mixing, and transferring to the column as in the preceding steps. Close the stopcock when drained.

Calculate the approximate amount of Binding Buffer needed to wash the STREAMLINE Protein A beads in the column using the data in Table 2.

TABLE 2

Binding Buffer Volume for Column Wash

| Quantity IgG (µg/ml) in Supernatant | Volume of Binding Buffer Required in Milliliters (ml) |
|---|---|
| >180-≦200 | 5 column washes total with 15.0 ml each |
| >160-≦180 | 5 column washes total with 15.0 ml each |
| >140-≦160 | 5 column washes total with 12.5 ml each |
| >120-≦140 | 5 column washes total with 12.5 ml each |
| >100-≦120 | 5 column washes total with 12.5 ml each |
| >80-≦100 | 5 column washes total with 10.0 ml each |
| >60-≦80 | 5 column washes total with 10.0 ml each |
| >40-≦60 | 5 column washes total with 7.5 ml each |
| >20-≦40 | 5 column washes total with 5.0 ml each |
| ≦20 | 5 column washes total with 5.0 ml each |

Wash the STREAMLINE Protein A beads in the column with the appropriate volume of Binding Buffer for the appropriate number of washes, continuing to collect the effluent into the "Column Wash-Post Binding" container. When completed, close the stopcock. Store the "Column Wash-Post Binding" container at 2° C. to 10° C.

Determine the Total Volumes of Elution Buffer and Neutralization Buffer needed to elute the STREAMLINE Protein A beads in the column from Table 3.

TABLE 3

Determination of Amount of Elution Buffer and Neutralization Buffer

| Quantity IgG µg/ml) in Supernatant | Total Volume of Elution Buffer Required (ml) | Total Volume of Neutralization Buffer Required (ml) | Volume of Elution Buffer Required per fraction (ml) | Volume of Neutralization Buffer Required per fraction (ml) |
|---|---|---|---|---|
| >180-≦200 | 72 | 7.2 | 12 | 1.2 |
| >160-≦180 | 66 | 6.6 | 11 | 1.1 |
| >140-≦160 | 60 | 6.0 | 10 | 1.0 |
| >120-≦140 | 54 | 5.4 | 9 | 0.9 |
| >100-≦120 | 48 | 4.8 | 8 | 0.8 |
| >80-≦100 | 42 | 4.2 | 7 | 0.7 |
| >60-≦80 | 36 | 3.6 | 6 | 0.6 |
| >40-≦60 | 27 | 2.7 | 4.5 | 0.45 |
| >20-≦40 | 21 | 2.1 | 3.5 | 0.35 |
| ≦20 | 12 | 1.2 | 2 | 0.2 |

Label 9 sterile conical centrifuge tubes "Eluted Antibody", Fraction # (1 through 9).

Place the appropriate volume of Neutralization Buffer required per fraction (as determined from Table "C" above) into each of the 9 "Eluted Antibody" fraction tubes and place securely under the column stopcock outlet.

Elute the STREAMLINE Protein A beads in the column fraction by fraction with the appropriate volume of Elution Buffer required per fraction (as determined from Table 3 above) while collecting the eluate into each of the "Eluted Antibody" tubes containing Neutralization Buffer.

When the elutions are complete, mix each "Eluted Antibody" fraction tube gently by swirling several times. Remove approximately 50 µl of fraction #3 and place on a pH test paper strip to ensure that the eluate has been neutralized to an approximate pH between 6.5 to 8.5. If required, add additional Neutralizing Buffer or Elution Buffer as needed to bring pH into range.

When pH evaluation is completed, perform an Absorbance Scan of a sample from each fraction at 280 nm-400 nm to determine the approximate concentration of IgG in the eluate prior to proceeding to the Dialysis Process.

Accept fractions as part of the Eluate Pool if the A280-A400 value is >0.200.

Reject fractions as part of the Eluate Pool if the A280-A400 value is <0.200.

Label a sterile conical centrifuge tube "Eluted Antibody," "Eluate Pool," and combine all fractions that were Accepted as part of the pool.

Perform an Absorbance Scan of a sample of the Eluate Pool to determine the approximate concentration of IgG in the eluate prior to proceeding to the Dialysis Process.

Estimate the volume of the Eluate Pool and calculate the approximate total mgs of IgG.

Volume of Eluate Pool: _____ mls× _____ IgG mg/ml= _____ Total mgs of IgG

Antibody dialysis

Remove the "Eluted Antibody" tube from 2° C. to 10° C.

Calculate the approximate length of Dialysis Tubing that will be needed to dialyze the antibody eluate using the approximate volume of eluate and the data in Table 4.

TABLE 4

Calculation of Length of Dialysis Tubing Needed

| Approximate Volume of Eluent (ml) | Volume/length Ratio of Dialysis Tubing | Approximate Length Needed for Eluent Sample (cm) | Head Space of 20% (cm) | Approximate Length Needed for Sample plus Headspace (cm) | Approximate Length Needed for Tie Off of Tubing (cm) | Approximate Total Length of Dialysis Tubing Needed (cm) |
|---|---|---|---|---|---|---|
| 39.6 | 2 | 20 | 4 | 24 | 15 | 63 |
| 36.3 | 2 | 18 | 4 | 22 | 15 | 59 |
| 33.0 | 2 | 17 | 3 | 20 | 15 | 55 |
| 29.7 | 2 | 15 | 3 | 18 | 15 | 51 |
| 26.4 | 2 | 13 | 3 | 16 | 15 | 47 |
| 23.1 | 2 | 12 | 2 | 14 | 15 | 43 |
| 19.8 | 2 | 10 | 2 | 12 | 15 | 39 |
| 14.85 | 2 | 7 | 1 | 9 | 15 | 33 |
| 11.55 | 2 | 6 | 1 | 7 | 15 | 29 |
| 6.6 | 2 | 3 | 1 | 4 | 15 | 23 |

Cut the appropriate length of dialysis tubing required. (multipurpose dialysis tubing, SPECTRA/PORT® 2 Regenerated Cellulose Membrane, 12,000-14,000 Dalton Molecular Weight Cutoff (MWCO), 16 mm Diameter, Spectrum Laboratories Inc., Cat. No. 132678)

Hydrate the dialysis membrane tubing in 1000 ml of $DIH_2O$ for >30 minutes.

Calculate the approximate volume of Dialysis Buffer needed to dialyze the antibody eluate using the data in Table 5.

TABLE 5

Volume of Dialysis Buffer Required

| Quantity IgG (µg/ml) in Supernatant | Final Volume of Eluted Antibody in Milliliters (ml) | Length of Dialysis Tubing Needed (cm) | Volume of Dialysis Buffer (1 × PBS) Needed in Liters |
|---|---|---|---|
| >180-≦200 | 39.6 ml | 63 cm | 3 complete changes of 4.0 Liters |
| >160-≦180 | 36.3 ml | 59 cm | 3 complete changes of 3.6 Liters |
| >140-≦160 | 33.0 ml | 55 cm | 3 complete changes of 3.3 Liters |
| >120-≦140 | 29.7 ml | 51 cm | 3 complete changes of 3.0 Liters |
| >100-≦120 | 26.4 ml | 47 cm | 3 complete changes of 2.6 Liters |
| >80-≦100 | 23.1 ml | 43 cm | 3 complete changes of 2.3 Liters |
| >60-≦80 | 19.8 ml | 39 cm | 3 complete changes of 1.9 Liters |
| >40-≦60 | 14.85 ml | 33 cm | 3 complete changes of 1.5 Liters |
| >20-≦40 | 11.55 ml | 29 cm | 3 complete changes of 1.2 Liters |
| ≦20 | 6.6 ml | 23 cm | 3 complete changes of 0.7 Liters |

Place the appropriate amount of Dialysis Buffer into a suitable sized plastic beaker. Label the beaker "Dialyzed Antibody." Add a clean stir bar and place the beaker on a stir plate inside a refrigerator or cold room at 2° C. to 10° C.

Rinse the dialysis tubing thoroughly in $DI-H_2O$. Tie two end knots approximately 7 cm from one end of the dialysis tubing and secure tightly.

Add approximately 5 ml of $DI-H_2O$ into the dialysis tubing.

Fill the dialysis tubing with the eluted antibody from the "Eluted Antibody" collection tube.

Tie two end knots approximately 7 cm from the remaining open end of the dialysis tubing and secure tightly. Ensure that the headspace is approximately that as derived from Table 4.

Place the filled and closed dialysis tubing into the dialysis reservoir with the appropriate volume of 1×PBS (from Table 5).

Cover the beaker with clean plastic wrap. Adjust the speed on the stir plate such that the dialysis sample spins freely, but is not pulled down into the vortex of the dialysate. Dialysis should take place at 2° C. to 10° C. with 3 buffer exchanges in total within a 24 hour period.

Antibody Filtration

Label a sterile collection tube "Dialyzed Antibody."

Remove the dialyzed sample tubing from the dialysis beaker. Cut the dialysis tubing open at one end and transfer the dialyzed sample into the "Dialyzed Antibody" centrifuge tube.

Label another sterile collection tube "Dialyzed Antibody."

Select a sterile Luer Lok syringe with adequate capacity to hold the final dialyszed volume.

Attach a syringe filter, ACRODISC® Syringe Filter to the opening of the syringe (0.2 µm HT membrane filter, TUFFRYN® Membrane, Low Protein binding, Gelman Laboratories, Cat. No. 4192). Remove the plunger from the syringe and while holding the syringe upright, transfer the dialyszed monoclonal antibody from the "Dialyzed Antibody" tube into the syringe. Replace the plunger.

Hold the syringe filter, ACRODISC® Syringe Filter over the opened, sterile, labeled "Purified Antibody" collection tube, and depress the syringe plunger to filter the purified antibody into the "Purified Antibody" tube.

When filtration is complete, cap the "Purified Antibody" tube and store at 2° C. to 10° C.

Determine concentration of purified monoclonal antibody using A280 procedure.

Example 4

General Method for Epitope Mapping

General Approach

Epitope mapping is performed to identify the linear amino acid sequence within an antigenic protein (i.e., the epitope) that is recognized by a particular monoclonal antibody. A general approach for epitope mapping requires the expression of the full-length protein, as well as various fragments (i.e., truncated forms) of the protein, generally in a heterologous expression system. These various recombinant proteins are then used to determine if the specific monoclonal antibody is capable of binding one or more of the truncated forms of the target protein. Through the use of reiterative truncation and the generation of recombinant proteins with overlapping amino acid regions, it is possible to identify the region that is recognized by the monoclonal antibody under investigation. Western blot analysis or ELISA is employed to determine if the specific monoclonal antibody under investigation is capable of binding one or more of the recombinant protein fragments. This approach can ultimately identify the peptide regions that contains the epitope and, in some cases, to refine the epitope precisely to an 8-15 amino acid sequence. An epitope can be a continuous linear sequence of 8-15 amino acids or it can be discontinuous with the antibody binding to a site on the protein composed of different sections of the peptide chain. Discontinuous epitopes generally cannot be mapped.

Construct Design and Creation

The first step in epitope mapping is the design of nested gene truncations. Frequently, the gene is divided into four equal parts for further analysis.

Gene Cloning Strategy

The general cloning strategy begins with PCR-based generation of the cloned gene fragments. In order to efficiently express the cloned fragment, especially when using small amino acid regions, the cloned fragment is expressed as a fusion protein, i.e. fused to another carrier protein that is stably expressed in the system. Green fluorescent protein (GFP) is frequently used as the carrier protein. GFP is included as a fusion partner to stabilize the truncation fragments and improve expression during the subsequent in vitro protein expression step. GFP also permits the tracking of fusion-protein expression using anti-GFP antibodies.

Cloning to create the GFP-protein construct is performed using either the mega-priming approach or through the use of plasmid cloning into the pScreen-GFP vector. Generally, the truncation fragments are fused to GFP and control sequences necessary for protein expression using a technique called megapriming.

Megapriming is the joining of two or more DNA fragments by annealing homologous regions at the end of the respective fragments and extending the annealed single-stranded DNA with a thermostable DNA polymerase. This process creates one large DNA fragment from two or more smaller fragments, linking them by their shared sequence. This large fragment is then amplified using standard PCR.

If megapriming cannot be used successfully, the truncation fragments can be cloned into a plasmid containing GFP and protein-expression control sequences. This cloning creates the GFP/fragment fusions necessary for epitope mapping. The remainder of the protocol can then proceed as described below.

Protein Expression

The expression constructs created by, for example, megapriming are then introduced into the Rapid Translation System (RTS). RTS is a cell-free protein expression system derived from E. coli lysates. This system permits rapid (3-4 hour) expression of proteins from DNA templates.

If RTS does not produce adequate levels of protein expression, then the truncation fragments will be cloned into the GFP protein-expression plasmid. These fusion plasmids are then transformed into an E. coli strain optimized for protein expression. Protein expression is induced in a growing culture of bacteria and, following outgrowth, the cells are lysed. The proteins in the complex cell lysate are then separated by polyacrylamide gel electrophoresis (PAGE), and the remainder of the protocol is the same as below.

Protein Detection and Epitope Mapping

Protein fragments produced by RTS are separated using PAGE and transferred onto nitrocellulose membranes. The membrane-bound proteins are then exposed to the antibody under investigation in solution. Antibody/protein binding is identified using calorimetric techniques known in the art.

Antibody binding of the full-length protein and some subset of the truncated protein fragments constitutes a positive result. If the absence of a particular section of the protein eliminates antibody binding, then the epitope lies on this fragment.

If the antibody to be mapped does not recognize protein bound to nitrocellulose membranes, then alternative methods for detecting antibody/protein interactions, such as, for example, ELISA or immunoprecipitation are used. Methods for detecting antibody/protein interactions are well known in the art.

Refining the Epitope Location

Since the above-described protocol will only narrow the location of the epitope down to approximately one-quarter of the protein, it is necessary to repeat the process on the quarter of the protein determined to contain the epitope in order to further resolve the location of the epitope. For a very large protein, it may be necessary to repeat this process two to three times to narrow the epitope down to 8-15 amino acids.

Example 5

Characterization of Epitope for MCM6 Monoclonal Antibody 9D4.3

Epitope mapping for MCM6 monoclonal antibody 9D4.3 was carried out essentially as described above in Example 4. Specifically, PCR was used to create four MCM6 gene truncations of the full-length MCM6 protein, followed by RTS to generate recombinant MCM6 protein fragments as GFP fusion proteins, and finally western blotting to detect antibody binding to specific MCM6 fragments. GFP was joined with the MCM6 gene truncations in a second round of PCR to ensure robust and stable expression in RTS.

The MCM6 protein fragments were analyzed by western blotting to identify fragment(s) that bind the 9D4.3 antibody. The western blot was probed directly with the 9D4.3 monoclonal antibody and a GFP antibody. A positive band was detected with the MCM6 truncation product designated as fragment 4. Fragment 4 was divided into five smaller fragments and the above process repeated to narrow the epitope.

The second set of MCM6 protein fragments was also analyzed by western blotting to identify fragment(s) that bind the 9D4.3 antibody. The western blot was probed directly with the 9D4.3 monoclonal antibody and a GFP antibody. Monoclonal antibody 9D4.3 was shown to bind to the region of MCM6 designated as 4-4. This fragment was again divided into six smaller fragments and the above process repeated to narrow the epitope.

The MCM6 protein fragments were again analyzed by western blotting as before. The western blot was probed directly with the 9D4.3 monoclonal antibody and a GFP antibody. A positive band was detected with the MCM6 fragment designated as 4-4-1. Additional fragments were generated to narrow the epitope region. Western blot analysis indicated that the epitope for the MCM6 antibody 9D4.3 comprises the amino acid sequence IDSEEELINKKRI (SEQ ID NO:5).

Results

Initial results showed that the epitope for the MCM6 monoclonal antibody 9D4.3 is located within the C-terminal region of the MCM6 protein. Continued truncations of the MCM6 protein showed that the epitope recognized by 9D4.3 is located within a thirteen amino acid region, specifically corresponding to amino acid residues 760-772 of SEQ ID NO:3 (IDSEEELINKKRI (SEQ ID NO:5)). Additional rounds of RTS may be able to refine the epitope location further.

Example 6

Characterization of Epitope for MCM7 Monoclonal Antibody 2E6.2

Epitope mapping for MCM7 monoclonal antibody 2E6.2 was performed essentially as described above in Example 5. The full-length MCM7 gene sequence (SEQ ID NO:1) was used as the starting sequence for designing gene fragments.

Results

The epitope for MCM7 monoclonal antibody 2E6.2 was determined to be located within the protein region comprising amino acid residues 127-138 of SEQ ID NO:1 (PAELMRRFELYF (SEQ ID NO:6)). Additional rounds of RTS may be able to refine the epitope location further.

That which is claimed:

1. A monoclonal antibody that is capable of specifically binding to MCM6, wherein the antibody is selected from the group consisting of:
   (a) the monoclonal antibody produced by the hybridoma cell line 9D4.3, deposited with the ATCC as Patent Deposit No. PTA-6911;
   (b) a monoclonal antibody that binds to an epitope capable of binding the monoclonal antibody produced by the hybridoma cell line 9D4.3;
   (c) a monoclonal antibody that binds to an epitope consisting of the amino acid sequence set forth in SEQ ID NO:5;
   (d) a monoclonal antibody that competes in a competitive binding assay with the monoclonal antibody produced by the hybridoma cell line 9D4.3; and,
   (e) a monoclonal antibody that is an antigen binding fragment of a monoclonal antibody of (a)-(d), wherein the fragment retains the capability of specifically binding to MCM6.

2. The hybridoma cell line 9D4.3, deposited with the ATCC as Patent Deposit No. PTA-6911.

3. A hybridoma cell line capable of producing a monoclonal antibody that is capable of specifically binding to MCM6, wherein the antibody is selected from the group consisting of:
   (a) the monoclonal antibody produced by the hybridoma cell line 9D4.3, deposited with the ATCC as Patent Deposit No. PTA-6911;
   (b) a monoclonal antibody that binds to an epitope capable of binding the monoclonal antibody produced by the hybridoma cell line 9D4.3;

(c) a monoclonal antibody that binds to an epitope consisting of the amino acid sequence set forth in SEQ ID NO:5; and (d) a monoclonal antibody that competes in a competitive binding assay with the monoclonal antibody produced by the hybridoma cell line 9D4.3.

4. A kit for diagnosing high-grade cervical disease comprising at least one monoclonal antibody according to claim 1.

5. The kit of claim 4, wherein the monoclonal antibody is the monoclonal antibody produced by the hybridoma cell line 9D4.3, deposited with the ATCC as Patent Deposit No. PTA-6911.

6. A kit comprising at least two monoclonal antibodies, wherein a first antibody is the MCM6 monoclonal antibody produced by the hybridoma cell line 9D4.3, deposited with the ATCC as Patent Deposit No. PTA-6911.

7. The kit of claim 6, wherein each antibody is provided as a separate antibody reagent or as an antibody cocktail.

8. The kit according to claim 4, wherein said kit further comprises a peroxidase blocking reagent, a protein blocking reagent, chemicals for the detection of antibody binding to a biomarker protein, a counterstain, a bluing agent, and instructions for diagnosing high-grade cervical disease.

9. The kit according to claim 4 further comprising reagents for Papanicolaou (Pap) staining.

10. A method for diagnosing high-grade cervical disease in a patient, the method comprising:
  a) obtaining a cervical sample from the patient;
  b) contacting the sample with at least one monoclonal antibody according to claim 1 that specifically binds to MCM6; and,
  c) detecting binding of the antibody to MCM6 to determine if MCM6 is overexpressed in said cervical sample compared to a normal cervical sample, wherein overexpression is indicative of high-grade cervical disease.

11. The method of claim 10, wherein the monoclonal antibody is the monoclonal antibody produced by the hybridoma cell line 9D4.3, deposited with the ATCC as Patent Deposit No. PTA-6911.

12. The method of claim 10 further comprising contacting the sample with at least one monoclonal antibody that specifically binds to MCM7.

13. The method according to claim 12, wherein the antibodies are contacted with the sample sequentially as individual antibody reagents or as an antibody cocktail.

* * * * *

SEQUENCE LISTING

```
<160> NUMBER OF SEQ ID NOS: 10

<210> SEQ ID NO 1
<211> LENGTH: 719
<212> TYPE: PRT
<213> ORGANISM: Homo sapiens

<400> SEQUENCE: 1

Met Ala Leu Lys Asp Tyr Ala Leu Glu Lys Glu Lys Val Lys Lys Phe
 1               5                  10                  15

Leu Gln Glu Phe Tyr Gln Asp Asp Glu Leu Gly Lys Lys Gln Phe Lys
                20                  25                  30

Tyr Gly Asn Gln Leu Val Arg Leu Ala His Arg Glu Gln Val Ala Leu
            35                  40                  45

Tyr Val Asp Leu Asp Asp Val Ala Glu Asp Pro Glu Leu Val Asp
        50                  55                  60

Ser Ile Cys Glu Asn Ala Arg Arg Tyr Ala Lys Leu Phe Ala Asp Ala
 65                  70                  75                  80

Val Gln Glu Leu Leu Pro Gln Tyr Lys Glu Arg Glu Val Val Asn Lys
                85                  90                  95

Asp Val Leu Asp Val Tyr Ile Glu His Arg Leu Met Met Glu Gln Arg
                100                 105                 110

Ser Arg Asp Pro Gly Met Val Arg Ser Pro Gln Asn Gln Tyr Pro Ala
            115                 120                 125

Glu Leu Met Arg Arg Phe Glu Leu Tyr Phe Gln Gly Pro Ser Ser Asn
        130                 135                 140

Lys Pro Arg Val Ile Arg Glu Val Arg Ala Asp Ser Val Gly Lys Leu
145                 150                 155                 160

Val Thr Val Arg Gly Ile Val Thr Arg Val Ser Glu Val Lys Pro Lys
                165                 170                 175

Met Val Val Ala Thr Tyr Thr Cys Asp Gln Cys Gly Ala Glu Thr Tyr
            180                 185                 190

Gln Pro Ile Gln Ser Pro Thr Phe Met Pro Leu Ile Met Cys Pro Ser
        195                 200                 205

Gln Glu Cys Gln Thr Asn Arg Ser Gly Gly Arg Leu Tyr Leu Gln Thr
        210                 215                 220

Arg Gly Ser Arg Phe Ile Lys Phe Gln Glu Met Lys Met Gln Glu His
225                 230                 235                 240

Ser Asp Gln Val Pro Val Gly Asn Ile Pro Arg Ser Ile Thr Val Leu
                245                 250                 255

Val Glu Gly Glu Asn Thr Arg Ile Ala Gln Pro Gly Asp His Val Ser
```

```
                260                 265                 270
Val Thr Gly Ile Phe Leu Pro Ile Leu Arg Thr Gly Phe Arg Gln Val
            275                 280                 285
Val Gln Gly Leu Leu Ser Glu Thr Tyr Leu Glu Ala His Arg Ile Val
            290                 295                 300
Lys Met Asn Lys Ser Glu Asp Asp Glu Ser Gly Ala Gly Glu Leu Thr
305                 310                 315                 320
Arg Glu Glu Leu Arg Gln Ile Ala Glu Asp Phe Tyr Glu Lys Leu
                325                 330                 335
Ala Ala Ser Ile Ala Pro Glu Ile Tyr Gly His Glu Asp Val Lys Lys
            340                 345                 350
Ala Leu Leu Leu Leu Val Gly Val Asp Gln Ser Pro Arg Gly
            355                 360                 365
Met Lys Ile Arg Gly Asn Ile Asn Ile Cys Leu Met Gly Asp Pro Gly
            370                 375                 380
Val Ala Lys Ser Gln Leu Leu Ser Tyr Ile Asp Arg Leu Ala Pro Arg
385                 390                 395                 400
Ser Gln Tyr Thr Thr Gly Arg Gly Ser Ser Gly Val Gly Leu Thr Ala
                405                 410                 415
Ala Val Leu Arg Asp Ser Val Ser Gly Glu Leu Thr Leu Glu Gly Gly
            420                 425                 430
Ala Leu Val Leu Ala Asp Gln Gly Val Cys Cys Ile Asp Glu Phe Asp
            435                 440                 445
Lys Met Ala Glu Ala Asp Arg Thr Ala Ile His Glu Val Met Glu Gln
450                 455                 460
Gln Thr Ile Ser Ile Ala Lys Ala Gly Ile Leu Thr Thr Leu Asn Ala
465                 470                 475                 480
Arg Cys Ser Ile Leu Ala Ala Ala Asn Pro Ala Tyr Gly Arg Tyr Asn
                485                 490                 495
Pro Arg Arg Ser Leu Glu Gln Asn Ile Gln Leu Pro Ala Ala Leu Leu
                500                 505                 510
Ser Arg Phe Asp Leu Leu Trp Leu Ile Gln Asp Arg Pro Asp Arg Asp
            515                 520                 525
Asn Asp Leu Arg Leu Ala Gln His Ile Thr Tyr Val His Gln His Ser
530                 535                 540
Arg Gln Pro Pro Ser Gln Phe Glu Pro Leu Asp Met Lys Leu Met Arg
545                 550                 555                 560
Arg Tyr Ile Ala Met Cys Arg Glu Lys Gln Pro Met Val Pro Glu Ser
                565                 570                 575
Leu Ala Asp Tyr Ile Thr Ala Ala Tyr Val Glu Met Arg Arg Glu Ala
                580                 585                 590
Trp Ala Ser Lys Asp Ala Thr Tyr Thr Ser Ala Arg Thr Leu Leu Ala
            595                 600                 605
Ile Leu Arg Leu Ser Thr Ala Leu Ala Arg Leu Arg Met Val Asp Val
            610                 615                 620
Val Glu Lys Glu Asp Val Asn Glu Ala Ile Arg Leu Met Glu Met Ser
625                 630                 635                 640
Lys Asp Ser Leu Leu Gly Asp Lys Gly Gln Thr Ala Arg Thr Gln Arg
                645                 650                 655
Pro Ala Asp Val Ile Phe Ala Thr Val Arg Glu Leu Val Ser Gly Gly
                660                 665                 670
Arg Ser Val Arg Phe Ser Glu Ala Glu Gln Arg Cys Val Ser Arg Gly
            675                 680                 685
```

```
Phe Thr Pro Ala Gln Phe Gln Ala Ala Leu Asp Glu Tyr Glu Glu Leu
690                 695                 700
Asn Val Trp Gln Val Asn Ala Ser Arg Thr Arg Ile Thr Phe Val
705                 710                 715

<210> SEQ ID NO 2
<211> LENGTH: 2821
<212> TYPE: DNA
<213> ORGANISM: Homo sapiens
<220> FEATURE:
<221> NAME/KEY: CDS
<222> LOCATION: (511)...(2670)

<400> SEQUENCE: 2
cgccccttcc cagccccaag ggtctaggat acagtctttg tagatgagcg ggtcccoctt      60 ggaggacaga atgaagaatt gggaaatcat ggccgttctg gagagtagac aagaagacgg     120
cgaaagtcgg gcctgccccg ccctgcggcc ccggaacaaa gaacgcgtg tgcgctggcc      180 ctttaagagc gattctcctc cgcccgcgcc agctcggacc gcgggaaacc cggcgcctgc     240 actacccgc cggagattc ccttccgacg cccgcaccgc ctccccgtca ctcattctag       300
gcccgcacgt tgattggctt gcggctagcg ggaggtgaag aaggccgcct tgtccgattg     360
gcccgcacgc agtggcgccg gtcacgtggg gggcgacgtt tcgcgccaat ttcggttggc     420
cggccacagt ccaccgcgcg gagattctca gcttccccag gagcaagacc tctgagcccg     480
ccaagcgcgg ccgcacggcc ctcggcagcg atg gca ctg aag gac tac gcg cta     534
                                   Met Ala Leu Lys Asp Tyr Ala Leu
                                    1               5 gag aag gaa aag gtt aag aag ttc tta caa gag ttc tac cag gat gat     582
Glu Lys Glu Lys Val Lys Lys Phe Leu Gln Glu Phe Tyr Gln Asp Asp
        10                  15                  20 gaa ctc ggg aag aag cag ttc aag tat ggg aac cag ttg gtt cgg ctg     630
Glu Leu Gly Lys Lys Gln Phe Lys Tyr Gly Asn Gln Leu Val Arg Leu
25                  30                  35                  40 gct cat cgg gaa cag gtg gct ctg tat gtg gac ctg gac gac gta gcc     678
Ala His Arg Glu Gln Val Ala Leu Tyr Val Asp Leu Asp Asp Val Ala
                45                  50                  55 gag gat gac ccc gag ttg gtg gac tca att tgt gag aat gcc agg cgc     726
Glu Asp Asp Pro Glu Leu Val Asp Ser Ile Cys Glu Asn Ala Arg Arg
            60                  65                  70 tac gcg aag ctc ttt gct gat gcc gta caa gag ctg ctg cct cag tac     774
Tyr Ala Lys Leu Phe Ala Asp Ala Val Gln Glu Leu Leu Pro Gln Tyr
        75                  80                  85 aag gag agg gaa gtg gta aat aaa gat gtc ctg gac gtt tac att gag     822
Lys Glu Arg Glu Val Val Asn Lys Asp Val Leu Asp Val Tyr Ile Glu
    90                  95                  100 cat cgg cta atg atg gag cag cgg agt cgg gac cct ggg atg gtc cga     870
His Arg Leu Met Met Glu Gln Arg Ser Arg Asp Pro Gly Met Val Arg
105                 110                 115                 120 agc ccc cag aac cag tac cct gct gaa ctc atg cgc aga ttt gag ctg     918
Ser Pro Gln Asn Gln Tyr Pro Ala Glu Leu Met Arg Arg Phe Glu Leu
                125                 130                 135 tat ttt caa ggc cct agc agc aac aag cct cgt gtg atc cgg gaa gtg     966
Tyr Phe Gln Gly Pro Ser Ser Asn Lys Pro Arg Val Ile Arg Glu Val
            140                 145                 150 cgg gct gac tct gtg ggg aag ttg gta act gtg cgt gga atc gtc act    1014
Arg Ala Asp Ser Val Gly Lys Leu Val Thr Val Arg Gly Ile Val Thr
        155                 160                 165 cgt gtc tct gaa gtc aaa ccc aag atg gtg gtg gcc act tac act tgt    1062
Arg Val Ser Glu Val Lys Pro Lys Met Val Val Ala Thr Tyr Thr Cys
    170                 175                 180
```

```
gac cag tgt ggg gca gag acc tac cag ccg atc cag tct ccc act ttc    1110
Asp Gln Cys Gly Ala Glu Thr Tyr Gln Pro Ile Gln Ser Pro Thr Phe
185                 190                 195                 200 atg cct ctg atc atg tgc cca agc cag gag tgc caa acc aac cgc tca    1158
Met Pro Leu Ile Met Cys Pro Ser Gln Glu Cys Gln Thr Asn Arg Ser
            205                 210                 215 gga ggg cgg ctg tat ctg cag aca cgg ggc tcc aga ttc atc aaa ttc    1206
Gly Gly Arg Leu Tyr Leu Gln Thr Arg Gly Ser Arg Phe Ile Lys Phe
        220                 225                 230 cag gag atg aag atg caa gaa cat agt gat cag gtg cct gtg gga aat    1254
Gln Glu Met Lys Met Gln Glu His Ser Asp Gln Val Pro Val Gly Asn
    235                 240                 245 atc cct cgt agt atc acg gtg ctg gta gaa gga gag aac aca agg att    1302
Ile Pro Arg Ser Ile Thr Val Leu Val Glu Gly Glu Asn Thr Arg Ile
250                 255                 260 gcc cag cct gga gac cac gtc agc gtc act ggt att ttc ttg cca atc    1350
Ala Gln Pro Gly Asp His Val Ser Val Thr Gly Ile Phe Leu Pro Ile
265                 270                 275                 280 ctg cgc act ggg ttc cga cag gtg gta cag ggt tta ctc tca gaa acc    1398
Leu Arg Thr Gly Phe Arg Gln Val Val Gln Gly Leu Leu Ser Glu Thr
            285                 290                 295 tac ctg gaa gcc cat cgg att gtg aag atg aac aag agt gag gat gat    1446
Tyr Leu Glu Ala His Arg Ile Val Lys Met Asn Lys Ser Glu Asp Asp
        300                 305                 310 gag tct ggg gct gga gag ctc acc agg gag gag ctg agg caa att gca    1494
Glu Ser Gly Ala Gly Glu Leu Thr Arg Glu Glu Leu Arg Gln Ile Ala
    315                 320                 325 gag gag gat ttc tac gaa aag ctg gca gct tca atc gcc cca gaa ata    1542
Glu Glu Asp Phe Tyr Glu Lys Leu Ala Ala Ser Ile Ala Pro Glu Ile
330                 335                 340 tac ggg cat gaa gat gtg aag aag gca ctg ctc ctg cta gtc ggg        1590
Tyr Gly His Glu Asp Val Lys Lys Ala Leu Leu Leu Leu Val Gly
345                 350                 355                 360 ggt gtg gac cag tct cct cga ggc atg aaa atc cgg ggc aac atc aac    1638
Gly Val Asp Gln Ser Pro Arg Gly Met Lys Ile Arg Gly Asn Ile Asn
            365                 370                 375 atc tgt ctg atg ggg gat cct ggt gtg gcc aag tct cag ctc ctg tca    1686
Ile Cys Leu Met Gly Asp Pro Gly Val Ala Lys Ser Gln Leu Leu Ser
        380                 385                 390 tac att gat cga ctg gcg cct cgc agc cag tac aca aca ggc cgg ggc    1734
Tyr Ile Asp Arg Leu Ala Pro Arg Ser Gln Tyr Thr Thr Gly Arg Gly
    395                 400                 405 tcc tca gga gtg ggg ctt acg gca gct gtg ctg aga gac tcc gtg agt    1782
Ser Ser Gly Val Gly Leu Thr Ala Ala Val Leu Arg Asp Ser Val Ser
410                 415                 420 gga gaa ctg acc tta gag ggt ggg gcc ctg gtg ctg gct gac cag ggt    1830
Gly Glu Leu Thr Leu Glu Gly Gly Ala Leu Val Leu Ala Asp Gln Gly
425                 430                 435                 440 gtg tgc tgc att gat gag ttc gac aag atg gct gag gcc gac cgc aca    1878
Val Cys Cys Ile Asp Glu Phe Asp Lys Met Ala Glu Ala Asp Arg Thr
            445                 450                 455 gcc atc cac gag gtc atg gag cag cag acc atc tcc att gcc aag gcc    1926
Ala Ile His Glu Val Met Glu Gln Gln Thr Ile Ser Ile Ala Lys Ala
        460                 465                 470 ggc att ctc acc aca ctc aat gcc cgc tgc tcc atc ctg gct gcc gcc    1974
Gly Ile Leu Thr Thr Leu Asn Ala Arg Cys Ser Ile Leu Ala Ala Ala
    475                 480                 485 aac cct gcc tac ggg cgc tac aac cct cgc cgc agc ctg gag cag aac    2022
Asn Pro Ala Tyr Gly Arg Tyr Asn Pro Arg Arg Ser Leu Glu Gln Asn
490                 495                 500
```

```
ata cag cta cct gct gca ctg ctc tcc cgg ttt gac ctc ctc tgg ctg      2070
Ile Gln Leu Pro Ala Ala Leu Leu Ser Arg Phe Asp Leu Leu Trp Leu
505                 510                 515                 520 att cag gac cgg ccc gac cga gac aat gac cta cgg ttg gcc cag cac      2118
Ile Gln Asp Arg Pro Asp Arg Asp Asn Asp Leu Arg Leu Ala Gln His
            525                 530                 535 atc acc tat gtg cac cag cac agc cgg cag ccc ccc tcc cag ttt gaa      2166
Ile Thr Tyr Val His Gln His Ser Arg Gln Pro Pro Ser Gln Phe Glu
        540                 545                 550 cct ctg gac atg aag ctc atg agg cgt tac ata gcc atg tgc cgc gag      2214
Pro Leu Asp Met Lys Leu Met Arg Arg Tyr Ile Ala Met Cys Arg Glu
    555                 560                 565 aag cag ccc atg gtg cca gag tct ctg gct gac tac atc aca gca gca      2262
Lys Gln Pro Met Val Pro Glu Ser Leu Ala Asp Tyr Ile Thr Ala Ala
570                 575                 580 tac gtg gag atg agg cga gag gct tgg gct agt aag gat gcc acc tat      2310
Tyr Val Glu Met Arg Arg Glu Ala Trp Ala Ser Lys Asp Ala Thr Tyr
585                 590                 595                 600 act tct gcc cgg acc ctg ctg gct atc ctg cgc ctt tcc act gct ctg      2358
Thr Ser Ala Arg Thr Leu Leu Ala Ile Leu Arg Leu Ser Thr Ala Leu
            605                 610                 615 gca cgt ctg aga atg gtg gat gtg gtg gag aaa gaa gat gtg aat gaa      2406
Ala Arg Leu Arg Met Val Asp Val Val Glu Lys Glu Asp Val Asn Glu
        620                 625                 630 gcc atc agg cta atg gag atg tca aag gac tct ctt cta gga gac aag      2454
Ala Ile Arg Leu Met Glu Met Ser Lys Asp Ser Leu Leu Gly Asp Lys
    635                 640                 645 ggg cag aca gct agg act cag aga cca gca gat gtg ata ttt gcc acc      2502
Gly Gln Thr Ala Arg Thr Gln Arg Pro Ala Asp Val Ile Phe Ala Thr
650                 655                 660 gtc cgt gaa ctg gtc tca ggg ggc cga agt gtc cgg ttc tct gag gca      2550
Val Arg Glu Leu Val Ser Gly Gly Arg Ser Val Arg Phe Ser Glu Ala
665                 670                 675                 680 gag cag cgc tgt gta tct cgt ggc ttc aca ccc gcc cag ttc cag gcg      2598
Glu Gln Arg Cys Val Ser Arg Gly Phe Thr Pro Ala Gln Phe Gln Ala
            685                 690                 695 gct ctg gat gaa tat gag gag ctc aat gtc tgg cag gtc aat gct tcc      2646
Ala Leu Asp Glu Tyr Glu Glu Leu Asn Val Trp Gln Val Asn Ala Ser
        700                 705                 710 cgg aca cgg atc act ttt gtc tga ttccagcctg cttgcaaccc tggggtcctc    2700
Arg Thr Arg Ile Thr Phe Val *
    715 ttgttccctg ctggcctgcc ccttgggaag gggcagtgat gcctttgagg ggaaggagga    2760 gccccctcttt ctcccatgct gcacttactc cttttgctaa taaaagtgtt tgtagattgt   2820 c                                                                    2821

<210> SEQ ID NO 3
<211> LENGTH: 821
<212> TYPE: PRT
<213> ORGANISM: Homo sapiens

<400> SEQUENCE: 3

Met Asp Leu Ala Ala Ala Ala Glu Pro Gly Ala Gly Ser Gln His Leu
1               5                   10                  15

Glu Val Arg Asp Glu Val Ala Glu Lys Cys Gln Lys Leu Phe Leu Asp
                20                  25                  30

Phe Leu Glu Glu Phe Gln Ser Ser Asp Gly Glu Ile Lys Tyr Leu Gln
        35                  40                  45
```

```
Leu Ala Glu Glu Leu Ile Arg Pro Glu Arg Asn Thr Leu Val Val Ser
 50                  55                  60

Phe Val Asp Leu Glu Gln Phe Asn Gln Gln Leu Ser Thr Thr Ile Gln
 65                  70                  75                  80

Glu Glu Phe Tyr Arg Val Tyr Pro Tyr Leu Cys Arg Ala Leu Lys Thr
                 85                  90                  95

Phe Val Lys Asp Arg Lys Glu Ile Pro Leu Ala Lys Asp Phe Tyr Val
                100                 105                 110

Ala Phe Gln Asp Leu Pro Thr Arg His Lys Ile Arg Glu Leu Thr Ser
            115                 120                 125

Ser Arg Ile Gly Leu Leu Thr Arg Ile Ser Gly Gln Val Val Arg Thr
130                 135                 140

His Pro Val His Pro Glu Leu Val Ser Gly Thr Phe Leu Cys Leu Asp
145                 150                 155                 160

Cys Gln Thr Val Ile Arg Asp Val Glu Gln Gln Phe Lys Tyr Thr Gln
                165                 170                 175

Pro Asn Ile Cys Arg Asn Pro Val Cys Ala Asn Arg Arg Phe Leu
            180                 185                 190

Leu Asp Thr Asn Lys Ser Arg Phe Val Asp Phe Gln Lys Val Arg Ile
            195                 200                 205

Gln Glu Thr Gln Ala Glu Leu Pro Arg Gly Ser Ile Pro Arg Ser Leu
210                 215                 220

Glu Val Ile Leu Arg Ala Glu Ala Val Glu Ser Ala Gln Ala Gly Asp
225                 230                 235                 240

Lys Cys Asp Phe Thr Gly Thr Leu Ile Val Val Pro Asp Val Ser Lys
                245                 250                 255

Leu Ser Thr Pro Gly Ala Arg Ala Glu Thr Asn Ser Arg Val Ser Gly
            260                 265                 270

Val Asp Gly Tyr Glu Thr Glu Gly Ile Arg Gly Leu Arg Ala Leu Gly
            275                 280                 285

Val Arg Asp Leu Ser Tyr Arg Leu Val Phe Leu Ala Cys Cys Val Ala
            290                 295                 300

Pro Thr Asn Pro Arg Phe Gly Gly Lys Glu Leu Arg Asp Glu Glu Gln
305                 310                 315                 320

Thr Ala Glu Ser Ile Lys Asn Gln Met Thr Val Lys Glu Trp Glu Lys
                325                 330                 335

Val Phe Glu Met Ser Gln Asp Lys Asn Leu Tyr His Asn Leu Cys Thr
            340                 345                 350

Ser Leu Phe Pro Thr Ile His Gly Asn Asp Glu Val Lys Arg Gly Val
            355                 360                 365

Leu Leu Met Leu Phe Gly Gly Val Pro Lys Thr Thr Gly Glu Gly Thr
            370                 375                 380

Ser Leu Arg Gly Asp Ile Asn Val Cys Ile Val Gly Asp Pro Ser Thr
385                 390                 395                 400

Ala Lys Ser Gln Phe Leu Lys His Val Glu Glu Phe Ser Pro Arg Ala
                405                 410                 415

Val Tyr Thr Ser Gly Lys Ala Ser Ser Ala Ala Gly Leu Thr Ala Ala
            420                 425                 430

Val Val Arg Asp Glu Glu Ser His Glu Phe Val Ile Glu Ala Gly Ala
            435                 440                 445

Leu Met Leu Ala Asp Asn Gly Val Cys Cys Ile Asp Glu Phe Asp Lys
            450                 455                 460

Met Asp Val Arg Asp Gln Val Ala Ile His Glu Ala Met Glu Gln Gln
465                 470                 475                 480
```

```
Thr Ile Ser Ile Thr Lys Ala Gly Val Lys Ala Thr Leu Asn Ala Arg
            485                 490                 495
Thr Ser Ile Leu Ala Ala Asn Pro Ile Ser Gly His Tyr Asp Arg
        500                 505                 510
Ser Lys Ser Leu Lys Gln Asn Ile Asn Leu Ser Ala Pro Ile Met Ser
            515                 520                 525
Arg Phe Asp Leu Phe Phe Ile Leu Val Asp Glu Cys Asn Glu Val Thr
        530                 535                 540
Asp Tyr Ala Ile Ala Arg Arg Ile Val Asp Leu His Ser Arg Ile Glu
545                 550                 555                 560
Glu Ser Ile Asp Arg Val Tyr Ser Leu Asp Asp Ile Arg Arg Tyr Leu
                565                 570                 575
Leu Phe Ala Arg Gln Phe Lys Pro Lys Ile Ser Lys Glu Ser Glu Asp
            580                 585                 590
Phe Ile Val Glu Gln Tyr Lys His Leu Arg Gln Arg Asp Gly Ser Gly
        595                 600                 605
Val Thr Lys Ser Ser Trp Arg Ile Thr Val Arg Gln Leu Glu Ser Met
610                 615                 620
Ile Arg Leu Ser Glu Ala Met Ala Arg Met His Cys Cys Asp Glu Val
625                 630                 635                 640
Gln Pro Lys His Val Lys Glu Ala Phe Arg Leu Leu Asn Lys Ser Ile
                645                 650                 655
Ile Arg Val Glu Thr Pro Asp Val Asn Leu Asp Gln Glu Glu Glu Ile
            660                 665                 670
Gln Met Glu Val Asp Glu Gly Ala Gly Gly Ile Asn Gly His Ala Asp
        675                 680                 685
Ser Pro Ala Pro Val Asn Gly Ile Asn Gly Tyr Asn Glu Asp Ile Asn
            690                 695                 700
Gln Glu Ser Ala Pro Lys Ala Ser Leu Arg Leu Gly Phe Ser Glu Tyr
705                 710                 715                 720
Cys Arg Ile Ser Asn Leu Ile Val Leu His Leu Arg Lys Val Glu Glu
                725                 730                 735
Glu Glu Asp Glu Ser Ala Leu Lys Arg Ser Glu Leu Val Asn Trp Tyr
            740                 745                 750
Leu Lys Glu Ile Glu Ser Glu Ile Asp Ser Glu Glu Leu Ile Asn
            755                 760                 765
Lys Lys Arg Ile Ile Glu Lys Val Ile His Arg Leu Thr His Tyr Asp
        770                 775                 780
His Val Leu Ile Glu Leu Thr Gln Ala Gly Leu Lys Gly Ser Thr Glu
785                 790                 795                 800
Gly Ser Glu Ser Tyr Glu Glu Asp Pro Tyr Leu Val Val Asn Pro Asn
                805                 810                 815
Tyr Leu Leu Glu Asp
            820

<210> SEQ ID NO 4
<211> LENGTH: 3769
<212> TYPE: DNA
<213> ORGANISM: Homo sapiens
<220> FEATURE:
<221> NAME/KEY: CDS
<222> LOCATION: (77)...(2542)

<400> SEQUENCE: 4
aaagctgcag cgtctggaaa aaagcgactt gtggcggtcg agcgtggcgc aggcgaatcc    60
```

```
tcggcactaa gcaaat atg gac ctc gcg gcg gca gcg gag ccg ggc gcc ggc      112
               Met Asp Leu Ala Ala Ala Ala Glu Pro Gly Ala Gly
                 1               5                  10 agc cag cac ctg gag gtc cgc gac gag gtg gcc gag aag tgc cag aaa        160
Ser Gln His Leu Glu Val Arg Asp Glu Val Ala Glu Lys Cys Gln Lys
         15                  20                  25 ctg ttc ctg gac ttc ttg gag gag ttt cag agc agc gat gga gaa att        208
Leu Phe Leu Asp Phe Leu Glu Glu Phe Gln Ser Ser Asp Gly Glu Ile
 30                  35                  40 aaa tac ttg caa tta gca gag gaa ctg att cgt cct gag aga aac aca        256
Lys Tyr Leu Gln Leu Ala Glu Glu Leu Ile Arg Pro Glu Arg Asn Thr
 45                  50                  55                  60 ttg gtt gtg agt ttt gtg gac ctg gaa caa ttt aac cag caa ctt tcc        304
Leu Val Val Ser Phe Val Asp Leu Glu Gln Phe Asn Gln Gln Leu Ser
             65                  70                  75 acc acc att caa gag gag ttc tat aga gtt tac cct tac ctg tgt cgg        352
Thr Thr Ile Gln Glu Glu Phe Tyr Arg Val Tyr Pro Tyr Leu Cys Arg
             80                  85                  90 gcc ttg aaa aca ttc gtc aaa gac cgt aaa gag atc cct ctt gcc aag        400
Ala Leu Lys Thr Phe Val Lys Asp Arg Lys Glu Ile Pro Leu Ala Lys
             95                 100                 105 gat ttt tat gtt gca ttc caa gac ctg cct acc aga cac aag att cga        448
Asp Phe Tyr Val Ala Phe Gln Asp Leu Pro Thr Arg His Lys Ile Arg
        110                 115                 120 gag ctc acc tca tcc aga att ggt ttg ctc act cgc atc agt ggg cag        496
Glu Leu Thr Ser Ser Arg Ile Gly Leu Leu Thr Arg Ile Ser Gly Gln
125                 130                 135                 140 gtg gtg cgg act cac cca gtt cac cca gag ctt gtg agc gga act ttt        544
Val Val Arg Thr His Pro Val His Pro Glu Leu Val Ser Gly Thr Phe
                145                 150                 155 ctg tgc ttg gac tgt cag aca gtg atc agg gat gta gaa cag cag ttc        592
Leu Cys Leu Asp Cys Gln Thr Val Ile Arg Asp Val Glu Gln Gln Phe
                160                 165                 170 aaa tac aca cag cca aac atc tgc cga aat cca gtt tgt gcc aac agg        640
Lys Tyr Thr Gln Pro Asn Ile Cys Arg Asn Pro Val Cys Ala Asn Arg
        175                 180                 185 agg aga ttc tta ctg gat aca aat aaa tca aga ttt gtt gat ttt caa        688
Arg Arg Phe Leu Leu Asp Thr Asn Lys Ser Arg Phe Val Asp Phe Gln
190                 195                 200 aag gtt cgt att caa gag acc caa gct gag ctt cct cga ggg agt atc        736
Lys Val Arg Ile Gln Glu Thr Gln Ala Glu Leu Pro Arg Gly Ser Ile
205                 210                 215                 220 ccc cgc agt tta gaa gta att tta agg gct gaa gct gtg gaa tca gct        784
Pro Arg Ser Leu Glu Val Ile Leu Arg Ala Glu Ala Val Glu Ser Ala
                225                 230                 235 caa gct ggt gac aag tgt gac ttt aca ggg aca ctg att gtt gtg cct        832
Gln Ala Gly Asp Lys Cys Asp Phe Thr Gly Thr Leu Ile Val Val Pro
                240                 245                 250 gac gtc tcc aag ctt agc aca cca gga gca cgt gca gaa act aat tcc        880
Asp Val Ser Lys Leu Ser Thr Pro Gly Ala Arg Ala Glu Thr Asn Ser
            255                 260                 265 cgt gtc agt ggt gtt gat gga tat gag aca gaa ggc att cga gga ctc        928
Arg Val Ser Gly Val Asp Gly Tyr Glu Thr Glu Gly Ile Arg Gly Leu
        270                 275                 280 cgg gcc ctt ggt gtt agg gac ctt tct tat agg ctg gtc ttt ctt gcc        976
Arg Ala Leu Gly Val Arg Asp Leu Ser Tyr Arg Leu Val Phe Leu Ala
285                 290                 295                 300 tgc tgt gtt gcg cca acc aac cca agg ttt ggg ggg aaa gag ctc aga       1024
Cys Cys Val Ala Pro Thr Asn Pro Arg Phe Gly Gly Lys Glu Leu Arg
                305                 310                 315
```

-continued

| | | |
|---|---|---|
| gat gag gaa cag aca gct gag agc att aag aac caa atg act gtg aaa<br>Asp Glu Glu Gln Thr Ala Glu Ser Ile Lys Asn Gln Met Thr Val Lys<br>320 325 330 | | 1072 |
| gaa tgg gag aaa gtg ttt gag atg agt caa gat aaa aat cta tac cac<br>Glu Trp Glu Lys Val Phe Glu Met Ser Gln Asp Lys Asn Leu Tyr His<br>335 340 345 | | 1120 |
| aat ctt tgt acc agc ctg ttc cct act ata cat ggc aat gat gaa gta<br>Asn Leu Cys Thr Ser Leu Phe Pro Thr Ile His Gly Asn Asp Glu Val<br>350 355 360 | | 1168 |
| aaa cgg ggt gtc ctg ctg atg ctc ttt ggt ggc gtt cca aag aca aca<br>Lys Arg Gly Val Leu Leu Met Leu Phe Gly Gly Val Pro Lys Thr Thr<br>365 370 375 380 | | 1216 |
| gga gaa ggg acc tct ctt cga ggg gac ata aat gtt tgc att gtt ggt<br>Gly Glu Gly Thr Ser Leu Arg Gly Asp Ile Asn Val Cys Ile Val Gly<br>385 390 395 | | 1264 |
| gac cca agt aca gct aag agc caa ttt ctc aag cac gtg gag gag ttc<br>Asp Pro Ser Thr Ala Lys Ser Gln Phe Leu Lys His Val Glu Glu Phe<br>400 405 410 | | 1312 |
| agc ccc aga gct gtc tac acc agt ggt aaa gcg tcc agt gct gct ggc<br>Ser Pro Arg Ala Val Tyr Thr Ser Gly Lys Ala Ser Ser Ala Ala Gly<br>415 420 425 | | 1360 |
| tta aca gca gct gtt gtg aga gat gaa gaa tct cat gag ttt gtc att<br>Leu Thr Ala Ala Val Val Arg Asp Glu Glu Ser His Glu Phe Val Ile<br>430 435 440 | | 1408 |
| gag gct gga gct ttg atg ttg gct gat aat ggt gtg tgt tgt att gat<br>Glu Ala Gly Ala Leu Met Leu Ala Asp Asn Gly Val Cys Cys Ile Asp<br>445 450 455 460 | | 1456 |
| gaa ttt gat aag atg gac gtg cgg gat caa gtt gct att cat gaa gct<br>Glu Phe Asp Lys Met Asp Val Arg Asp Gln Val Ala Ile His Glu Ala<br>465 470 475 | | 1504 |
| atg gaa cag cag acc ata tcc atc act aaa gca gga gtg aag gct act<br>Met Glu Gln Gln Thr Ile Ser Ile Thr Lys Ala Gly Val Lys Ala Thr<br>480 485 490 | | 1552 |
| ctg aac gcc cgg acg tcc att ttg gca gca gca aac cca atc agt gga<br>Leu Asn Ala Arg Thr Ser Ile Leu Ala Ala Ala Asn Pro Ile Ser Gly<br>495 500 505 | | 1600 |
| cac tat gac aga tca aaa tca ttg aaa cag aat ata aat ttg tca gct<br>His Tyr Asp Arg Ser Lys Ser Leu Lys Gln Asn Ile Asn Leu Ser Ala<br>510 515 520 | | 1648 |
| ccc atc atg tcc cga ttc gat ctc ttc ttt atc ctt gtg gat gaa tgt<br>Pro Ile Met Ser Arg Phe Asp Leu Phe Phe Ile Leu Val Asp Glu Cys<br>525 530 535 540 | | 1696 |
| aat gag gtt aca gat tat gcc att gcc agg cgc ata gta gat ttg cat<br>Asn Glu Val Thr Asp Tyr Ala Ile Ala Arg Arg Ile Val Asp Leu His<br>545 550 555 | | 1744 |
| tca aga att gag gaa tca att gat cgt gtc tat tcc ctc gat gat atc<br>Ser Arg Ile Glu Glu Ser Ile Asp Arg Val Tyr Ser Leu Asp Asp Ile<br>560 565 570 | | 1792 |
| aga aga tat ctt ctc ttt gca aga cag ttt aaa ccc aag att tcc aaa<br>Arg Arg Tyr Leu Leu Phe Ala Arg Gln Phe Lys Pro Lys Ile Ser Lys<br>575 580 585 | | 1840 |
| gag tca gag gac ttc att gtg gag caa tat aaa cat ctc cgc cag aga<br>Glu Ser Glu Asp Phe Ile Val Glu Gln Tyr Lys His Leu Arg Gln Arg<br>590 595 600 | | 1888 |
| gat ggt tct gga gtg acc aag tct tca tgg agg att aca gtg cga cag<br>Asp Gly Ser Gly Val Thr Lys Ser Ser Trp Arg Ile Thr Val Arg Gln<br>605 610 615 620 | | 1936 |
| ctt gag agc atg att cgt ctc tct gaa gct atg gct cgg atg cac tgc<br>Leu Glu Ser Met Ile Arg Leu Ser Glu Ala Met Ala Arg Met His Cys<br>625 630 635 | | 1984 |

|  |  |
|---|---:|
| tgt gat gag gtc caa cct aaa cat gtg aag gaa gct ttc cgg tta ctg<br>Cys Asp Glu Val Gln Pro Lys His Val Lys Glu Ala Phe Arg Leu Leu<br>640 645 650 | 2032 |
| aat aaa tca atc atc cgt gtg gaa aca cct gat gtc aat cta gat caa<br>Asn Lys Ser Ile Ile Arg Val Glu Thr Pro Asp Val Asn Leu Asp Gln<br>655 660 665 | 2080 |
| gag gaa gag atc cag atg gag gta gat gag ggt gct ggt ggc atc aat<br>Glu Glu Glu Ile Gln Met Glu Val Asp Glu Gly Ala Gly Gly Ile Asn<br>670 675 680 | 2128 |
| ggt cat gct gac agc cct gct cct gtg aac ggg atc aat ggc tac aat<br>Gly His Ala Asp Ser Pro Ala Pro Val Asn Gly Ile Asn Gly Tyr Asn<br>685 690 695 700 | 2176 |
| gaa gac ata aat caa gag tct gct ccc aaa gcc tcc tta agg ctg ggc<br>Glu Asp Ile Asn Gln Glu Ser Ala Pro Lys Ala Ser Leu Arg Leu Gly<br>705 710 715 | 2224 |
| ttc tct gag tac tgc cga atc tct aac ctt att gtg ctt cac ctc aga<br>Phe Ser Glu Tyr Cys Arg Ile Ser Asn Leu Ile Val Leu His Leu Arg<br>720 725 730 | 2272 |
| aag gtg gaa gaa gaa gag gac gag tca gca tta aag agg agc gag ctt<br>Lys Val Glu Glu Glu Glu Asp Glu Ser Ala Leu Lys Arg Ser Glu Leu<br>735 740 745 | 2320 |
| gtt aac tgg tac ttg aag gaa atc gaa tca gag ata gac tct gaa gaa<br>Val Asn Trp Tyr Leu Lys Glu Ile Glu Ser Glu Ile Asp Ser Glu Glu<br>750 755 760 | 2368 |
| gaa ctt ata aat aaa aaa aga atc ata gag aaa gtt att cat cga ctc<br>Glu Leu Ile Asn Lys Lys Arg Ile Ile Glu Lys Val Ile His Arg Leu<br>765 770 775 780 | 2416 |
| aca cac tat gat cat gtt cta att gag ctc acc cag gct gga ttg aaa<br>Thr His Tyr Asp His Val Leu Ile Glu Leu Thr Gln Ala Gly Leu Lys<br>785 790 795 | 2464 |
| ggc tcc aca gag gga agt gag agc tat gaa gaa gat ccc tac ttg gta<br>Gly Ser Thr Glu Gly Ser Glu Ser Tyr Glu Glu Asp Pro Tyr Leu Val<br>800 805 810 | 2512 |
| gtt aac cct aac tac ttg ctc gaa gat tga gatagtgaaa gtaactgacc<br>Val Asn Pro Asn Tyr Leu Leu Glu Asp *<br>815 820 | 2562 |
| agagctgagg aactgtggca cagcacctcg tggcctggag cctggctgga gctctgctag | 2622 |
| ggacagaagt gtttctggaa gtgatgcttc caggatttgt tttcagaaac aagaattgag | 2682 |
| ttgatggtcc tatgtgtcac attcatcaca ggtttcatac caaacacaggc ttcagcactt | 2742 |
| cctttggtgt gtttcctgtc ccagtgaagt tggaaccaaa taatgtgtag tctctataac | 2802 |
| caataccttt gttttcatgt gtaagaaaag gcccattact tttaaggtat gtgctgtcct | 2862 |
| attgagcaaa taacttttt tcaattgcca gctactgctt ttattcatca aaataaaata | 2922 |
| acttgttctg aagttgtcta ttggatttct ttctactgta ccctgattat tacttccatc | 2982 |
| tacttctgaa tgtgagactt tccctttttg cttaacctgg agtgaagagg tagaactgtg | 3042 |
| gtattatgga tgaggtttct atgagaagga gtcattagag aactcatatg aaagctagag | 3102 |
| gccttagaga tgactttcca aggttaattc cagttgtttt ttttttttt taagtttata | 3162 |
| aaagtttatt atactttttt aaaattactc tttagtaatt tattttactt ctgtgtccta | 3222 |
| agggtaattt ctcaggattg ttttcaaatt gcttttttag gggaaatagg tcatttgcta | 3282 |
| tattacaagc aatccccaaa ttttatggtc ttccaggaaa agttattacc gtttatgata | 3342 |
| ctaacagttc ctgagactta gctatgatca gtatgttcat gaggtggagc agttcctgtg | 3402 |
| ttgcagcttt taacaacaga tggcattcat taaatcacaa agtatgttaa aggtcacaaa | 3462 |
| agcaaaataa ctgtctgagg ctaaggccca cgtgggacag tctaataccc atgagtactc | 3522 |

```
aacttgcctt gatgtctgag ctttccagtg caatgtgaat ttgagcagcc agaaatctat    3582
tagtagaaag caagacagat taatataggt taaaacaatg atttaaatat gtttctccca    3642
ataattatct ctttccctgg aatcaacttg tatgaaacct tgtcaaaatg tactccacaa    3702
gtatgtacaa ttaagtattt taaaaataaa tggcaaacat taaaaacaaa aaaaaaaaaa    3762
aaaaaaa                                                              3769

<210> SEQ ID NO 5
<211> LENGTH: 13
<212> TYPE: PRT
<213> ORGANISM: Artificial Sequence
<220> FEATURE:
<223> OTHER INFORMATION: Epitope for MCM6 monoclonal antibody 9D4.3

<400> SEQUENCE: 5

Ile Asp Ser Glu Glu Glu Leu Ile Asn Lys Lys Arg Ile
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Epitope for MCM7 monoclonal antibody 2E6.2

<400> SEQUENCE: 6

Pro Ala Glu Leu Met Arg Arg Phe Glu Leu Tyr Phe
1               5                   10

<210> SEQ ID NO 7
<211> LENGTH: 555
<212> TYPE: DNA
<213> ORGANISM: Artificial Sequence
<220> FEATURE:
<223> OTHER INFORMATION: Nucleotide sequence for a hexahistidine-tagged
      N-terminal fragment of MCM7

<400> SEQUENCE: 7
atggcactga aggactacgc gctagagaag gaaaaggtta agaagttctt acaagagttc     60
taccaggatg atgaactcgg gaagaagcag ttcaagtatg gaaccagtt ggttcggctg     120 gctcatcggg aacaggtggc tctgtatgtg gacctggacg acgtagccga ggatgacccc    180
gagttggtgg actcaatttg tgagaatgcc aggcgctacg cgaagctctt tgctgatgcc    240
gtacaagagc tgctgcctca gtacaaggag agggaagtgg taaataaaga tgtcctggac    300
gtttacattg agcatcggct aatgatggag cagcggagtc gggaccctgg gatggtccga    360
agcccccaga accagtaccc tgctgaactc atgcgcagat ttgagctgta ttttcaaggc    420
cctagcagca acaagcctcg tgtgatccgg gaagtgcggg ctgactctgt ggggaagttg    480
gtaactgtgc gtggaatcgt cactcgtgtc tctgaagtca aacccaaggg tggtcatcat    540
catcatcatc attga                                                    555

<210> SEQ ID NO 8
<211> LENGTH: 184
<212> TYPE: PRT
<213> ORGANISM: Artificial Sequence
<220> FEATURE:
<223> OTHER INFORMATION: Amino acid sequence for the hexahistidine-
      tagged N-terminal fragment of MCM7 encoded by SEQ ID NO:7

<400> SEQUENCE: 8

Met Ala Leu Lys Asp Tyr Ala Leu Glu Lys Glu Lys Val Lys Lys Phe
1               5                   10                  15
```

```
Leu Gln Glu Phe Tyr Gln Asp Asp Glu Leu Gly Lys Lys Gln Phe Lys
             20                  25                  30

Tyr Gly Asn Gln Leu Val Arg Leu Ala His Arg Glu Gln Val Ala Leu
         35                  40                  45

Tyr Val Asp Leu Asp Asp Val Ala Glu Asp Pro Glu Leu Val Asp
     50                  55                  60

Ser Ile Cys Glu Asn Ala Arg Arg Tyr Ala Lys Leu Phe Ala Asp Ala
 65                  70                  75                  80

Val Gln Glu Leu Leu Pro Gln Tyr Lys Glu Arg Glu Val Val Asn Lys
                 85                  90                  95

Asp Val Leu Asp Val Tyr Ile Glu His Arg Leu Met Met Glu Gln Arg
             100                 105                 110

Ser Arg Asp Pro Gly Met Val Arg Ser Pro Gln Asn Gln Tyr Pro Ala
         115                 120                 125

Glu Leu Met Arg Arg Phe Glu Leu Tyr Phe Gln Gly Pro Ser Ser Asn
     130                 135                 140

Lys Pro Arg Val Ile Arg Glu Val Arg Ala Asp Ser Val Gly Lys Leu
145                 150                 155                 160

Val Thr Val Arg Gly Ile Val Thr Arg Val Ser Glu Val Lys Pro Lys
                 165                 170                 175

Gly Gly His His His His His His
            180

<210> SEQ ID NO 9
<211> LENGTH: 2590
<212> TYPE: DNA
<213> ORGANISM: Artificial Sequence
<220> FEATURE:
<223> OTHER INFORMATION: Nucleotide sequence for a FLAG-tagged MCM6
      polypeptide

<400> SEQUENCE: 9
cgagctcgga tccactagta acggccgcca gtgtgctgga attcgccctt ttgctagccc      60
accatggacc tcgcggcggc agcggagccg ggcgccggca gccagcacct ggaggtccgc     120
gacgaggtgg ccgagaagtg ccagaaactg ttcctggact tcttggagga gtttcagagc     180
agcgatggag aaattaaata cttgcaatta gcagaggaac tgattcgtcc tgagagaaac     240
acattggttg tgagttttgt ggacctggaa caatttaacc agcaactttc caccaccatt     300
caagaggagt tctatagagt ttacccttac ctgtgtcggg ccttgaaaac attcgtcaaa     360
gaccgtaaag agatccctct tgccaaggat tttttatgttg cattccaaga cctgcctacc     420
agacacaaga ttcgagagct cacctcatcc agaattggtt tgctcactcg catcagtggg     480
caggtggtgc ggactcaccc agttcaccca gagcttgtga gcggaacttt tctgtgcttg     540
gactgtcaga cagtgatcag ggatgtagaa cagcagttca atacacaca gccaaacatc     600 tgccgaaatc cagtttgtgc caacaggagg agattcttac tggatacaaa taatcaaga     660 tttgttgatt ttcaaaaggt tcgtattcaa gagacccaag ctgagcttcc tcgagggagt     720 atccccgca gtttagaagt aattttaagg gctgaagctg tggaatcagc tcaagctggt     780
gacaagtgtg actttacagg acactgatt gttgtgcctg acgtctccaa gcttagcaca     840
ccaggagcac gtgcagaaac taattcccgt gtcagtggtt gatggata tgagacagaa     900 ggcattcgag gactccgggc ccttggtgtt agggaccttt cttataggct ggtctttctt     960
gcctgctgtg ttgcgccaac caacccaagg ttttgggggga aagagctcag agatgaggaa    1020
cagacagctg agagcattaa gaaccaaatg actgtgaaag aatgggagaa agtgtttgag    1080
```

```
atgagtcaag ataaaaatct ataccacaat ctttgtacca gcctgttccc tactatacat   1140
ggcaatgatg aagtaaaacg gggtgtcctg ctgatgctct ttggtggcgt tccaaagaca   1200
acaggagaag ggacctctct tcgaggggac ataaatgttt gcattgttgg tgacccaagt   1260
acagctaaga gccaatttct caagcacgtg gaggagttca gcccagagc tgtctacacc    1320 agtggtaaag cgtccagtgc tgctggctta acagcagctg ttgtgagaga tgaagaatct   1380
catgagtttg tcattgaggc tggagctttg atgttggctg ataatggtgt gtgttgtatt   1440
gatgaatttg ataagatgga cgtgcgggat caagttgcta ttcatgaagc tatggaacag   1500
cagaccatat ccatcactaa agcaggagtg aaggctactc tgaacgcccg gacgtccatt   1560
ttggcagcag caaacccaat cagtggacac tatgacagat caaaatcatt gaaacagaat   1620
ataaatttgt cagctcccat catgtcccga ttcgatctct tctttatcct tgtggatgaa   1680
tgtaatgagg ttacagatta tgccattgcc aggcgcatag tagatttgca ttcaagaatt   1740
gaggaatcaa ttgatcgtgt ctattccctc gatgatatca aagatatct tctctttgca    1800 agacagttta aacccaagat ttccaaagag tcagaggact tcattgtgga gcaatataaa   1860
catctccgcc agagagatgg ttctggagtg accaagtctt catggaggat tacagtgcga   1920
cagcttgaga gcatgattcg tctctctgaa gctatggctc ggatgcactg ctgtgatgag   1980
gtccaaccta acatgtgaa ggaagctttc cggttactga ataaatcaat catccgtgtg    2040
gaaacacctg atgtcaatct agatcaagag gaagagatcc agatggaggt agatgagggt   2100
gctggtggca tcaatggtca tgctgacagc cctgctcctg tgaacgggat caatggctac   2160
aatgaagaca taaatcaaga gtctgctccc aaagcctcct taaggctggg cttctctgag   2220
tactgccgaa tctctaacct tattgtgctt caccctcagaa aggtggaaga agaaggac    2280 gagtcagcat taaagaggag cgagcttgtt aactggtact gaaggaaat cgaatcagag    2340 atagactctg aagaagaact tataaataaa aaagaatca tagagaaagt tattcatcga    2400
ctcacacact atgatcatgt tctaattgag ctcacccagg ctggattgaa aggctccaca   2460
gagggaagtg agagctatga agaagatccc tacttggtag ttaaccctaa ctacttgctc   2520
gaagatttcg aactgcagaa aagggcgaat tctgcagata tccatcacac tggcggccgc   2580
tcgagcatgc                                                         2590
```

<210> SEQ ID NO 10
<211> LENGTH: 821
<212> TYPE: PRT
<213> ORGANISM: Artificial Sequence
<220> FEATURE:
<223> OTHER INFORMATION: Amino acid sequence for the FLAG-tagged MCM6
      polypeptide encoded by SEQ ID NO:9

<400> SEQUENCE: 10

Met Asp Leu Ala Ala Ala Ala Glu Pro Gly Ala Gly Ser Gln His Leu
1               5                   10                  15

Glu Val Arg Asp Glu Val Ala Glu Lys Cys Gln Lys Leu Phe Leu Asp
            20                  25                  30

Phe Leu Glu Glu Phe Gln Ser Ser Asp Gly Glu Ile Lys Tyr Leu Gln
        35                  40                  45

Leu Ala Glu Glu Leu Ile Arg Pro Glu Arg Asn Thr Leu Val Val Ser
    50                  55                  60

Phe Val Asp Leu Glu Gln Phe Asn Gln Gln Leu Ser Thr Thr Ile Gln
65                  70                  75                  80

Glu Glu Phe Tyr Arg Val Tyr Pro Tyr Leu Cys Arg Ala Leu Lys Thr

```
                85                  90                  95
Phe Val Lys Asp Arg Lys Glu Ile Pro Leu Ala Lys Asp Phe Tyr Val
            100                 105                 110
Ala Phe Gln Asp Leu Pro Thr Arg His Lys Ile Arg Glu Leu Thr Ser
            115                 120                 125
Ser Arg Ile Gly Leu Leu Thr Arg Ile Ser Gly Gln Val Val Arg Thr
            130                 135                 140
His Pro Val His Pro Glu Leu Val Ser Gly Thr Phe Leu Cys Leu Asp
145                 150                 155                 160
Cys Gln Thr Val Ile Arg Asp Val Glu Gln Gln Phe Lys Tyr Thr Gln
                165                 170                 175
Pro Asn Ile Cys Arg Asn Pro Val Cys Ala Asn Arg Arg Phe Leu
            180                 185                 190
Leu Asp Thr Asn Lys Ser Arg Phe Val Asp Phe Gln Lys Val Arg Ile
            195                 200                 205
Gln Glu Thr Gln Ala Glu Leu Pro Arg Gly Ser Ile Pro Arg Ser Leu
            210                 215                 220
Glu Val Ile Leu Arg Ala Glu Ala Val Glu Ser Ala Gln Ala Gly Asp
225                 230                 235                 240
Lys Cys Asp Phe Thr Gly Thr Leu Ile Val Val Pro Asp Val Ser Lys
                245                 250                 255
Leu Ser Thr Pro Gly Ala Arg Ala Glu Thr Asn Ser Arg Val Ser Gly
            260                 265                 270
Val Asp Gly Tyr Glu Thr Glu Gly Ile Arg Gly Leu Arg Ala Leu Gly
            275                 280                 285
Val Arg Asp Leu Ser Tyr Arg Leu Val Phe Leu Ala Cys Cys Val Ala
            290                 295                 300
Pro Thr Asn Pro Arg Phe Gly Gly Lys Glu Leu Arg Asp Glu Glu Gln
305                 310                 315                 320
Thr Ala Glu Ser Ile Lys Asn Gln Met Thr Val Lys Glu Trp Glu Lys
                325                 330                 335
Val Phe Glu Met Ser Gln Asp Lys Asn Leu Tyr His Asn Leu Cys Thr
            340                 345                 350
Ser Leu Phe Pro Thr Ile His Gly Asn Asp Glu Val Lys Arg Gly Val
            355                 360                 365
Leu Leu Met Leu Phe Gly Gly Val Pro Lys Thr Thr Gly Glu Gly Thr
            370                 375                 380
Ser Leu Arg Gly Asp Ile Asn Val Cys Ile Val Gly Asp Pro Ser Thr
385                 390                 395                 400
Ala Lys Ser Gln Phe Leu Lys His Val Glu Glu Phe Ser Pro Arg Ala
            405                 410                 415
Val Tyr Thr Ser Gly Lys Ala Ser Ser Ala Ala Gly Leu Thr Ala Ala
            420                 425                 430
Val Val Arg Asp Glu Glu Ser His Glu Phe Val Ile Glu Ala Gly Ala
            435                 440                 445
Leu Met Leu Ala Asp Asn Gly Val Cys Cys Ile Asp Glu Phe Asp Lys
            450                 455                 460
Met Asp Val Arg Asp Gln Val Ala Ile His Glu Ala Met Glu Gln Gln
465                 470                 475                 480
Thr Ile Ser Ile Thr Lys Ala Gly Val Lys Ala Thr Leu Asn Ala Arg
                485                 490                 495
Thr Ser Ile Leu Ala Ala Ala Asn Pro Ile Ser Gly His Tyr Asp Arg
            500                 505                 510
```

-continued

```
Ser Lys Ser Leu Lys Gln Asn Ile Asn Leu Ser Ala Pro Ile Met Ser
        515                 520                 525

Arg Phe Asp Leu Phe Phe Ile Leu Val Asp Glu Cys Asn Glu Val Thr
    530                 535                 540

Asp Tyr Ala Ile Ala Arg Arg Ile Val Asp Leu His Ser Arg Ile Glu
545                 550                 555                 560

Glu Ser Ile Asp Arg Val Tyr Ser Leu Asp Asp Ile Arg Arg Tyr Leu
                565                 570                 575

Leu Phe Ala Arg Gln Phe Lys Pro Lys Ile Ser Lys Glu Ser Glu Asp
                580                 585                 590

Phe Ile Val Glu Gln Tyr Lys His Leu Arg Gln Arg Asp Gly Ser Gly
            595                 600                 605

Val Thr Lys Ser Ser Trp Arg Ile Thr Val Arg Gln Leu Glu Ser Met
        610                 615                 620

Ile Arg Leu Ser Glu Ala Met Ala Arg Met His Cys Cys Asp Glu Val
625                 630                 635                 640

Gln Pro Lys His Val Lys Glu Ala Phe Arg Leu Leu Asn Lys Ser Ile
                645                 650                 655

Ile Arg Val Glu Thr Pro Asp Val Asn Leu Asp Gln Glu Glu Glu Ile
                660                 665                 670

Gln Met Glu Val Asp Glu Gly Ala Gly Gly Ile Asn Gly His Ala Asp
            675                 680                 685

Ser Pro Ala Pro Val Asn Gly Ile Asn Gly Tyr Asn Glu Asp Ile Asn
        690                 695                 700

Gln Glu Ser Ala Pro Lys Ala Ser Leu Arg Leu Gly Phe Ser Glu Tyr
705                 710                 715                 720

Cys Arg Ile Ser Asn Leu Ile Val Leu His Leu Arg Lys Val Glu Glu
                725                 730                 735

Glu Glu Asp Glu Ser Ala Leu Lys Arg Ser Glu Leu Val Asn Trp Tyr
            740                 745                 750

Leu Lys Glu Ile Glu Ser Glu Ile Asp Ser Glu Glu Leu Ile Asn
        755                 760                 765

Lys Lys Arg Ile Ile Glu Lys Val Ile His Arg Leu Thr His Tyr Asp
        770                 775                 780

His Val Leu Ile Glu Leu Thr Gln Ala Gly Leu Lys Gly Ser Thr Glu
785                 790                 795                 800

Gly Ser Glu Ser Tyr Glu Glu Asp Pro Tyr Leu Val Val Asn Pro Asn
                805                 810                 815

Tyr Leu Leu Glu Asp
            820
```